(12) United States Patent
Jacobson et al.

(10) Patent No.: US 12,378,248 B2
(45) Date of Patent: Aug. 5, 2025

(54) A1 ADENOSINE RECEPTOR AGONISTS AND METHODS OF USE THEREOF

(71) Applicant: The United States of America, as represented by the Secretary, Department of Health and Human Services, Bethesda, MD (US)

(72) Inventors: Kenneth A. Jacobson, Silver Spring, MD (US); Dilip K. Tosh, Rockville, MD (US); Marc L. Reitman, Potomac, MD (US); Oksana Gavrilova, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1036 days.

(21) Appl. No.: 17/299,890

(22) PCT Filed: Dec. 6, 2019

(86) PCT No.: PCT/US2019/064844
§ 371 (c)(1),
(2) Date: Jun. 4, 2021

(87) PCT Pub. No.: WO2020/118139
PCT Pub. Date: Jun. 11, 2020

(65) Prior Publication Data
US 2022/0024926 A1 Jan. 27, 2022

Related U.S. Application Data

(60) Provisional application No. 62/776,528, filed on Dec. 7, 2018.

(51) Int. Cl.
*C07D 473/40* (2006.01)
*C07D 249/10* (2006.01)
*C07D 471/04* (2006.01)

(52) U.S. Cl.
CPC ......... *C07D 473/40* (2013.01); *C07D 249/10* (2013.01); *C07D 471/04* (2013.01)

(58) Field of Classification Search
None
See application file for complete search history.

(56) References Cited

U.S. PATENT DOCUMENTS 8,916,570 B2   12/2014   Jacobson et al.
9,181,253 B2   11/2015   Jacobson et al.
(Continued)

FOREIGN PATENT DOCUMENTS

WO   WO-2019232554 A2 * 12/2019 ............. A61K 31/52

OTHER PUBLICATIONS

Clark RE, Christlieb I, Sanmarco M, Diaz-Perez R, Dammann JF, Zipser ME. Relationship of hypoxia to arrhythmia and cardiac conduction hemorrhage: an experimental study. Circulation. 1963;27:742-7. (Year: 1963).*
(Continued)

*Primary Examiner* — Jeffrey S Lundgren
*Assistant Examiner* — Anthony Joseph Seitz
(74) *Attorney, Agent, or Firm* — Leydig, Voit & Mayer, Ltd.

(57) ABSTRACT

Disclosed are compounds of the formulas (I), (II), and (II): which are $A_1$ adenosine receptor agonists, pharmaceutical compositions comprising such compounds, and a method of use of these compounds, wherein Y, $R^1$-$R^6$, $R^{10}$-$R^{15}$, and $R^{20}$-$R^{22}$ are as defined in the specification. These compounds are selective to the $A_1$ adenosine receptor, and are contemplated for use in the treatment or prevention of a
(Continued)

number of diseases or conditions, for example, for inducing and/or maintaining a hypothermic and/or hypometabolic state for treatment of a mammal.

29 Claims, 6 Drawing Sheets

(56) References Cited

U.S. PATENT DOCUMENTS

| | | | |
|---|---|---|---|
| 9,963,450 B2 | 5/2018 | Jacobson et al. | |
| 10,577,368 B2 | 3/2020 | Jacobson et al. | |
| 2012/0252823 A1* | 10/2012 | Jacobson | A61P 25/24 |
| | | | 514/263.4 |

OTHER PUBLICATIONS

NIH, National Heart, Lung, and Blood Institute, What Causes a Heart Attack? Published Dec. 16, 2014, Accessed via Wayback Machine, https://web.archive.org/web/20150218075735/http://www.nhlbi.nih.gov/health/health-topics/topics/heartattack/causes (Year: 2014).*
Berge et al., "Pharmaceutical Salts," Review Article from *Journal of Pharmaceutical Sciences*, 66(1): 1-19 (Jan. 1977).
Boison, "Adenosine as a neuromodulator in neurological diseases," *Current Opinion in Pharmacology*, 8(1): 2-7 (Feb. 2008) Author Manuscript.
Carlin et al., "Hypothermia in mouse cause by adenosine $A_1$ and $A_3$ receptor agonists and AMP via three distinct mechanisms," *Neuropharmacology*, 114: 101-113 (Mar. 2017) Author Manuscript.
Deluca et al., "Parenteral Drug-Delivery Systems," *Pharmaceutics and Pharmacy Practice*, (Banker et al., eds.) 238-250 (J. B. Lippincott Co., Philadelphia, PA, 1982).
Korean Intellectual Property Office, International Search Report in International Patent Application No. PCT/US2019/064844, mailed Mar. 24, 2020 (7 pp.).
Korean Intellectual Property Office, Written Opinion in International Patent Application No. PCT/US2019/064844, mailed Mar. 24, 2020 (7 pp.).
Gallo-Rodriguez et al., "Structure-Activity Relationships of $N^6$-Benzyladenosine-5'-uronamides as $A_3$-Selective Adenosine Agonists," *Journal of Medicinal Chemistry*, 37(5): 636-646 (Mar. 1994) Author Manuscript.
Gao et al., "$N^6$-Substituted adenosine derivatives: selectivity, efficacy, and species differences at $A_3$ adenosine receptors," *Biochemical Pharmacology*, 65(10): 1675-1684 (May 2003) Author Manuscript.
Gao et al., "A1 Adenosine Receptor Agonists, Antagonists, and Allosteric Modulators. In: Borea P., Varani K., Gessi S., Merighi S., Vincenzi F. (eds) The Adenosine Receptors. The Receptors," *Springer*, 34: 59-89 (2018).
Giorgi et al., "Adenosine $A_1$ modulators: a patent update (2008 to present)," *Expert Opinion on Therapeutic Patents*, 23(9): 1109-1121 (Sep. 2013).
Greene et al., "The adenosine-mediated, neuronal-glial, homeostatic sleep response," *Current Opinion Neurobiology*, 44: 236-242 (Jun. 2017) Author Manuscript.
Jacobson et al., "A Neoceptor Approach to Unraveling Microscopic Interactions between the Human $A_{2A}$ Adenosine Receptor and Its Agonists," *Chemistry & Biology*, 12(2): 237-247 (Feb. 2005) Author Manuscript.
Jacobson et al., "Semi-Rational Design of (N)-Methanocarba Nucleosides as Dual Acting $A_1$ and $A_3$Adenosine Receptor Agonists: Novel Prototypes for Cardioprotection," *Journal of Medicinal Chemistry*, 48(26): 8103-8107 (Dec. 2005) Author Manuscript.
Jinka et al., "Translating Drug-Induced Hibernation to Therapeutic Hypothermia," *ACS Chemical Neuroscience*, 6(6): 899-904 (Jun. 2015) Author Manuscript.

Kiesman et al., "$A_1$ Adenosine Receptor Antagonists, Agonists, and Allosteric Enhancers," *Handbook of Experimental Pharmacology*, 193: 25-58 (May 2009).
Knutsen et al., "NV-Substituted Adenosines as Novel Neuroprotective A1 Agonists with Diminished Hypotensive Effects," *Journal of Medicinal Chemistry*, 42: 3463-3477 (1999).
Kuang et al., "Enantioselective syntheses of carbocyclic ribavirin and its analogs: linear versus convergent approaches," *Tetrahedron Letters*, 41(49): 9575-9579 (Dec. 2000).
Kusachi et al., "Dog coronary artery adenosine receptor: structure of the N6-alkyl subregion," *Journal of Medicinal Chemistry*, 28(11): 1636-1643 (Nov. 1985).
Laughlin et al., "Precise Control of Target Temperature Using $N^6$-Cyclohexyladenosine and Real-Time Control of Surface Temperature," *Therapeutic Hypothermia and Temperature Management*, 8(2): 108-116 (2018).
Luongo et al., "5'-Chloro-5'-deoxy-(±)-ENBA, a Potent and Selective Adenosine $A_1$ Receptor Agonist, Alleviates Neuropathic Pain in Mice Through Functional Glial and Microglial Changes without Affecting Motor or Cardiovascular Functions," *Molecules*, 17: 13712-13726 (2012).
Mor et al., "INO-8875, a Highly Selective $A_1$ Adenosine Receptor Agonist: Evaluation of Chronotropic, Dromotropic, and Hemodynamic Effects in Rats," *The Journal of Pharmacology and Experimental Therapeutics*, 344: 59-67 (Jan. 2013).
Merkel et al., "Cardiovascular and antilipolytic effects of the adenosine agonist GR7923," *Pharmacology*, 51(4): 224-236 (Oct. 1995).
Müller et al., "Recent developments in adenosine receptor ligands and their potential as novel drugs," *Biochimica et Biophysica Acta*, 1808(5): 1290-1308 (May 2011) Author Manuscript.
Petrelli et al., "Exploring the Role of NV6-Substituents in Potent Dual Acting 5'-C-Ethyltetrazolyladenosine Derivatives: Synthesis, Binding, Functional Assays, and Antinociceptive Effects in Mice," *Journal of Medicinal Chemistry*, 60(10): 4327-4341 (May 2017) Author Manuscript.
Remingtons' Pharmaceutical Sciences, 18th ed., p. 1445 (1990).
Rodriguez et al., "Structure-Based Screening of Uncharted Chemical Space for Atypical Adenosine Receptor Agonists," *ACS Chemical Biology*, 11(10): 2763-2772 (Oct. 2016) Author Manuscript.
Serchov et al., "Increased Signaling via Adenosine $A_1$ Receptors, Sleep Deprivation, Imipramine, and Ketamine Inhibit Depressive-like Behavior via Induction of Homer1a," *Neuron*, 87(3): 549-562 (Aug. 2015) Author Manuscript.
Sawynok, "Adenosine receptor targets for pain," *Neuroscience*, 338: 1-18 (Dec. 2016).
Schenone et al., "$A_1$ receptors ligands: past, present and future trends," *Current Topics in Medical Chemistry*, 10(9): 878-901 (2010).
Schulte et al., "Adenosine A receptors are necessary for protection of the murine heart by remote, delayed adaptation to ischaemia," *Acta physiologica Scandinavica*, 182(2): 133-143 (Oct. 2004).
Tosh et al., "Optimization of Adenosine 5'-Carboxamide Derivatives as Adenosine Receptor Agonists Using Structure-Based Ligand Design and Fragment Screening," *Journal of Medicinal Chemistry*, 55(9): 4297-4308 (May 2012).
Tosh et al., "Structural Sweet Spot for $A_1$ Adenosine Receptor Activation by Truncated (N)- Methanocarba Nucleosides: Receptor Docking and Potent Anticonvulsant Activity," *Journal of Medicinal Chemistry*, 55(18): 8075-8090 (Sep. 2012).
Tosh et al., "Structure-Based Scaffold Repurposing for G Protein-Coupled Receptors: Transformation of Adenosine Derivatives into $5HT_{2B}/5HT_{2C}$ Serotonin Receptor Antagonists," *Journal of Medicinal Chemistry*, 59(24): 11006-11026 (Dec. 2016).
Tosh et al., "Design and in vivo Characterization of $A_1$ Adenosine Receptor Agonists in the Native Ribose and Conformationally-Constrained (N)-Methanocarba Series," *Journal of Medicinal Chemistry*, 62(3): 1502-1522 (Feb. 2019).
Tozzi et al., "Purinergic Receptors in Adipose Tissue as Potential Targets in Metabolic Disorders," *Frontiers in Pharmacology*, 8: 1-8 (Nov. 2017).

(56) References Cited

OTHER PUBLICATIONS

Trissel, "Intravenous Infusion Solutions," *ASHP Handbook on Injectable Drugs*, (Trissel, ed.) 622-630 (American Society of Hospital Pharmacists, Inc., Bethesda, MD, 1986).

Tupone et al., "Central Activation of the A1 Adenosine Receptor (A1AR) Induces a Hypothermic, Torpor-Like State in the Rat," *The Journal of Neuroscience*, 33(36): 14512-14525 (Sep. 2013).

Van Der Hoeven et al., "A Role for the Low-Affinity $A_{2B}$ Adenosine Receptor in Regulating Superoxide Generation by Murine Neutrophils," *The Journal of Pharmacology and Experimental Therapeutics*, 338(3): 1004-1012 (Jun. 2011).

\* cited by examiner

MRS5474

A1 ADENOSINE RECEPTOR AGONISTS AND METHODS OF USE THEREOF

CROSS REFERENCE TO RELATED APPLICATIONS

This patent application is the U.S. national phase of International Patent Application No. PCT/US2019/064844, filed on Dec. 6, 2019 and claims the benefit of U.S. Provisional Patent Application No. 62/776,528, filed Dec. 7, 2018, the disclosures of which are incorporated herein by reference in their entirety for all purposes.

STATEMENT REGARDING FEDERALLY SPONSORED RESEARCH OR DEVELOPMENT

This invention was made with Government support under Grant Numbers ZIA DK031117-28, ZIA DK075063, and NIA AG000356 awarded by the National Institutes of Health. The Government has certain rights in this invention.

BACKGROUND OF THE INVENTION

The $A_1$ adenosine receptor ($A_1AR$) is coupled to the inhibition of adenylyl cyclase through the Gi protein and also acts on ion channels and MAP kinases (1, 2). $A_1AR$ agonists are desired for their antiarrhythmic, antilipolytic, antinociceptive, cerebroprotective, cardioprotective, antidepressant, sleep-enhancing and antiseizure properties (1-7). Beneficial peripheral effects of $A_1AR$ agonists include protection in acute and chronic pain (8, 9) or as antilipolytic agents (10). The induction of mouse hypothermia through brain $A_1AR$ activation that is independent of peripheral $A_3AR$ activation was recently described (14). Pharmacologically-induced hypothermia has potential clinical applications, such as cerebroprotection in brain ischemia, but most $A_1AR$ agonists are unsuitable as clinical candidates because of their cardiovascular effects (1, 4, 11-13). Thus, there is a need for novel $A_1AR$ agonists that are well-tolerated for a variety of clinical applications, but with diminished side effects.

BRIEF SUMMARY OF THE INVENTION

The invention provides a compound of formula (I):

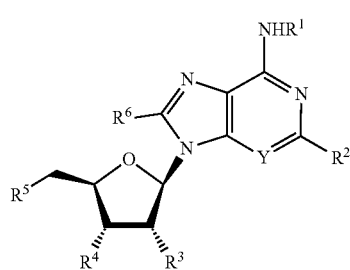

(I)

wherein Y is N or CH,
$R^1$ is dicyclobutylmethyl, dicyclopentylmethyl, dicyclohexylmethyl, dicycloheptylmethyl, dicyclooctylmethyl, dicyclononylmethyl or dicyclodecylmethyl,
$R^2$ and $R^6$ are independently selected from hydrogen, halo, $C_1$-$C_6$ alkyl, $C_2$-$C_6$ alkenyl, $C_2$-$C_6$ alkynyl, heteroaryl, $C_1$-$C_6$ alkylthio, $C_1$-$C_6$ alkoxy, and $C_1$-$C_6$ alkylamino;
$R^3$ and $R^4$ are independently selected from hydrogen, hydroxyl, amino, mercapto, ureido, $C_1$-$C_6$ alkyl carbonylamino, hydroxy $C_1$-$C_6$ alkyl, and hydrazinyl; and
$R^5$ is selected from hydrogen, hydroxyl, halo, $C_1$-$C_3$ alkyl aminocarbonyl, hydroxy $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;
or a pharmaceutically acceptable salt thereof.

The invention also provides a compound of formula (II):

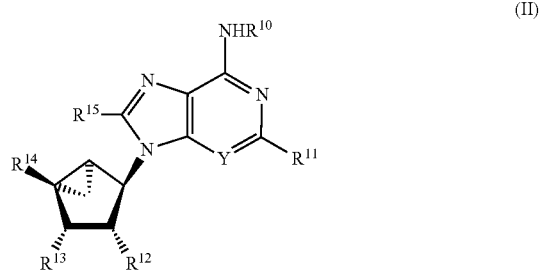

(II)

wherein Y is N or CH,
$R^{10}$ is dicyclobutylmethyl, dicyclopentylmethyl, dicyclohexylmethyl, dicycloheptylmethyl, dicyclooctylmethyl, dicyclononylmethyl, dicyclodecylmethyl, or endo-2-norbornyl,
$R^{11}$ and $R^{15}$ are independently selected from hydrogen, halo, $C_1$-$C_6$ alkyl, $C_2$-$C_6$ alkenyl, $C_2$-$C_6$ alkynyl, heteroaryl, $C_1$-$C_6$ alkylthio, $C_1$-$C_6$ alkoxy, and $C_1$-$C_6$ alkylamino;
$R^{12}$ and $R^{13}$ are independently selected from hydrogen, hydroxyl, amino, mercapto, ureido, $C_1$-$C_6$ alkyl carbonylamino, hydroxy $C_1$-$C_6$ alkyl, and hydrazinyl; and
$R^{14}$ is selected from hydrogen, $C_1$-$C_3$ alkoxycarbonyl, $C_1$-$C_3$ alkyl aminocarbonyl, hydroxy $C_1$-$C_3$ alkyl aminocarbonyl, di($C_1$-$C_3$ alkyl) aminocarbonyl, $C_3$-$C_8$ cycloalkyl aminocarbonyl, $C_1$-$C_3$ alkylthio $C_1$-$C_3$ alkyl, $C_6$-$C_{10}$ arylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl, wherein the aryl portion of arylthio is optionally substituted with one or more substituents selected from halo and $C_1$-$C_3$ alkoxy;
or a pharmaceutically acceptable salt thereof.

The invention further provides a compound of formula (III):

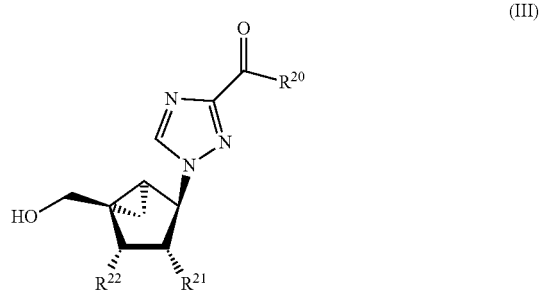

(III)

wherein $R^{20}$ is amino, $C_1$-$C_3$ alkoxy, $C_1$-$C_3$ alkylamino, hydroxy $C_1$-$C_3$ alkylamino, di($C_1$-$C_3$ alkyl)amino, or $C_3$-$C_8$ cycloalkylamino, and $R^{21}$ and $R^{22}$ are independently selected from hydrogen, hydroxyl, amino, mercapto, ureido, $C_1$-$C_6$ alkyl carbonylamino, hydroxy $C_1$-$C_6$ alkyl, and hydrazinyl, or a pharmaceutically acceptable salt thereof.

The invention also provides a method of inducing and/or maintaining a hypothermic and/or hypometabolic state for treatment of a mammal, comprising administering to the mammal an effective amount of a compound or salt of any one of the compounds of the invention.

The invention further provides a method of inducing and/or maintaining a hypothermic and/or hypometabolic state in a mammal, comprising administering to the mammal an effective amount of a compound or salt of any one of the compounds of the invention, wherein the mammal is subjected to a surgical procedure.

The invention additionally provides a method of treating a disease or disorder in a mammal in need thereof, wherein the disease or disorder is selected from chronic pain, acute pain, diabetes, cardiac arrhythmia, myocardial infarction, depression, and brain ischemia, comprising administering to the mammal an effective amount of a compound or salt of any one of the compounds of the invention.

BRIEF DESCRIPTION OF THE SEVERAL VIEWS OF THE DRAWING(S)

FIG. 1A shows graphically functional activity of agonists 2 and 7, in stimulation of guanine nucleotide binding at the $rA_1AR$ from recombinant $A_1AR$ membrane preparations from CHO-K1 cells, Perkin Elmer, as compared to 2.

FIG. 1B shows graphically the effects of agonists 7 and 16 in inhibition of cAMP accumulation at $hA_3AR$ (in $A_3AR$-expressing CHO cells, treated with 10 µM forskolin, compared to 16). 100% value is defined as effect of 1 µM 16.

FIG. 2A-2J show graphically the effects of nucleoside derivatives on body temperature (Tb) in WT (C57BL/6J male) or AR-KO mice. Compound 9 (FIG. A-E) or 29 (FIG. F-J), both at 3 mg/kg, ip., and vehicle were dosed in wild-type mice (WT, FIGS. 2A and 2F), or mice lacking $A_1AR$ (FIG. 2B, 2G), $A_3AR$ (FIG. C, 2H), or both $A_1AR$ and $A_3AR$ (FIG. 2D, 2I). FIGS. E and J show Tb during the first 60 min after dosing, mean±SEM, N=4 to 12/group. t-Test (2-tailed, paired or unpaired as appropriate) P values for vehicle vs compound, within genotype.

FIG. 3 shows the effect of compounds 9 and 24 on mouse Tb.

FIG. 4A shows the average immobility time in the tail suspension test exhibited by mice treated i.p. with saline (control), 10 mg/kg fluoxetine (FLX), or 0.3 mg/kg of compound 12, 1 mg/kg of compound 12, or 2 mg/kg of compound 12.

DETAILED DESCRIPTION OF THE INVENTION

Figure 1A:
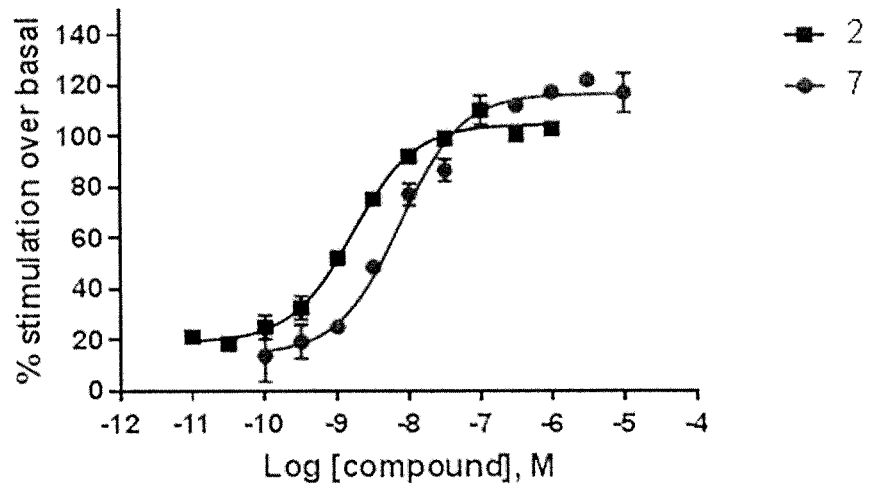
Figure 1B:
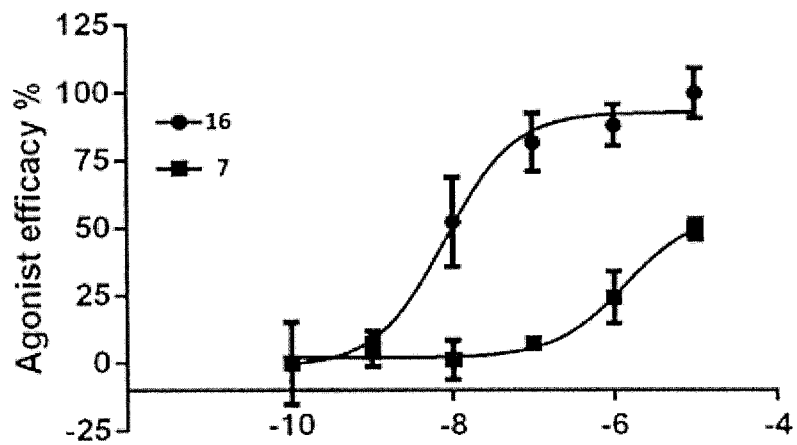
Figure 2A:
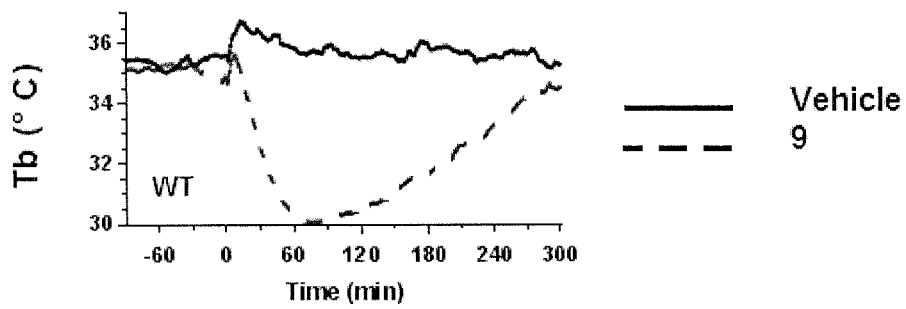
Figure 2B:
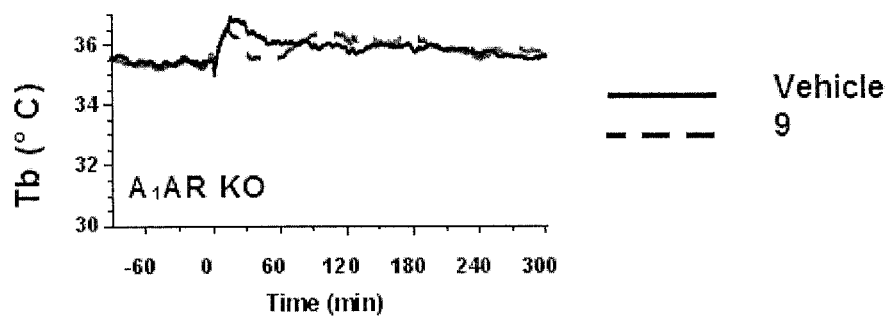
Figure 2C:
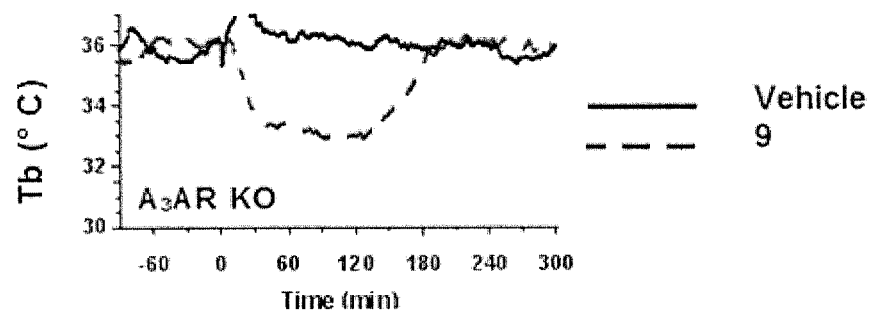
Figure 2D:
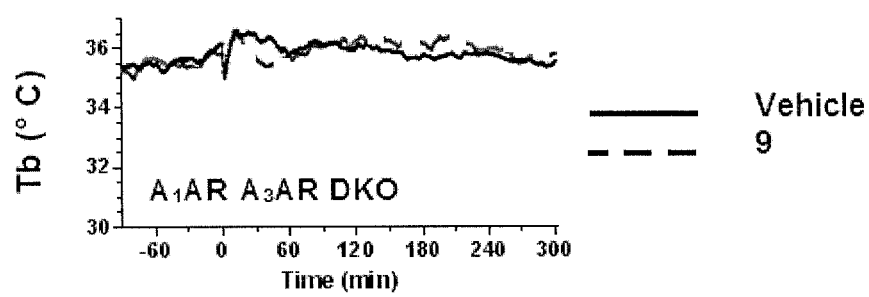
Figure 2E:
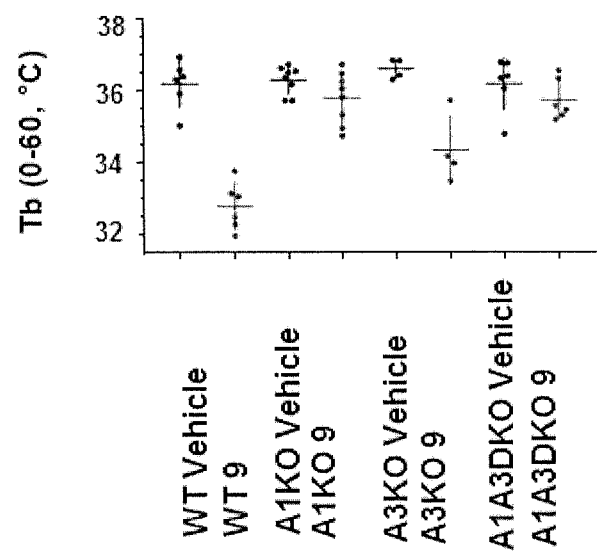
Figure 2F:
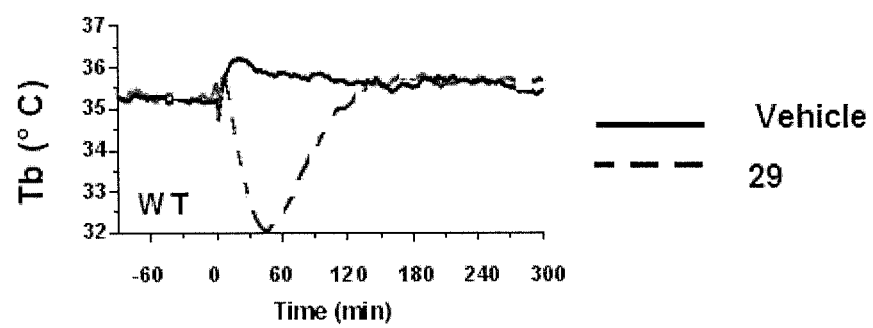
Figure 2G:
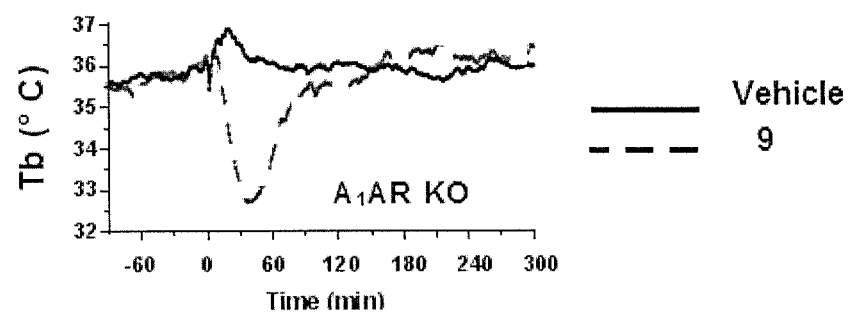
Figure 2H:
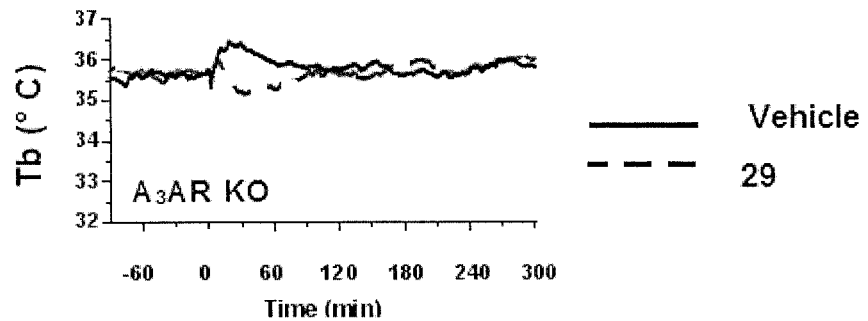
Figure 2I:
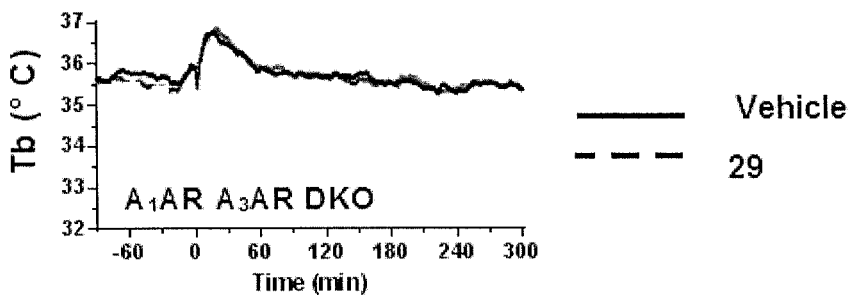
Figure 2J:
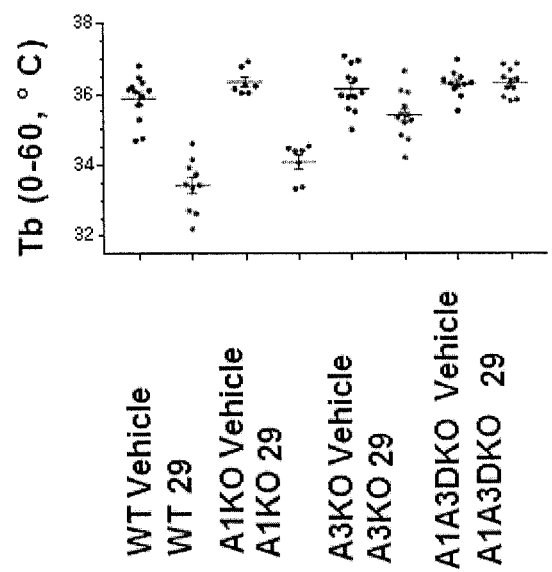

In an embodiment, the invention provides a compound of formula (I):

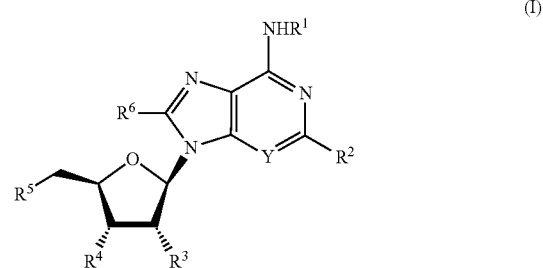

wherein Y is N or CH, $R^1$ is dicyclobutylmethyl, dicyclopentylmethyl, dicyclohexylmethyl, dicycloheptylmethyl, dicyclooctylmethyl, dicyclononylmethyl or dicyclodecylmethyl, $R^2$ and $R^6$ are independently selected from hydrogen, halo, $C_1$-$C_6$ alkyl, $C_2$-$C_6$ alkenyl, $C_2$-$C_6$ alkynyl, heteroaryl, $C_1$-$C_6$ alkylthio, $C_1$-$C_6$ alkoxy, and $C_1$-$C_6$ alkylamino;

$R_3$ and $R_4$ are independently selected from hydrogen, hydroxyl, amino, mercapto, ureido, $C_1$-$C_6$ alkyl carbonylamino, hydroxy $C_1$-$C_6$ alkyl, and hydrazinyl; and $R_5$ is selected from hydrogen, hydroxyl, halo, $C_1$-$C_3$ alkyl aminocarbonyl, hydroxy $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;

or a pharmaceutically acceptable salt thereof.

In an aspect, $R^6$ is hydrogen.

In certain aspects, Y is N.

In an aspect, $R^3$ and $R^4$ are both hydroxyl.

In certain aspects, $R^5$ is selected from hydroxyl and halo.

In certain aspects, $R^2$ is H or chloro.

In certain aspects, $R^1$ is dicyclobutylmethyl.

In certain preferred aspects, the compound is:

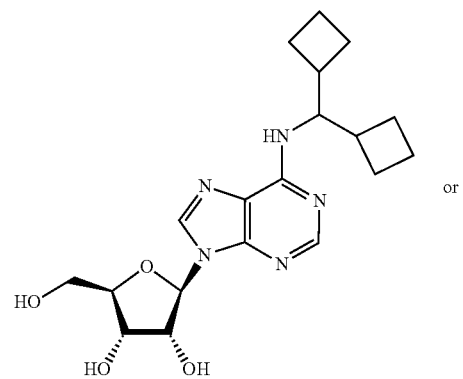

or

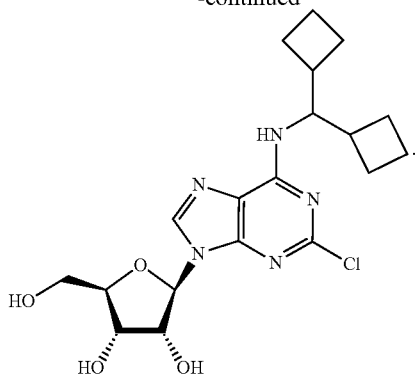

In an aspect, the invention provides a compound of formula (II):

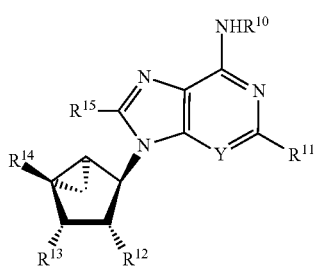

(II)

wherein Y is N or CH,

R$^{10}$ is dicyclobutylmethyl, dicyclopentylmethyl, dicyclohexylmethyl, dicycloheptylmethyl, dicyclooctylmethyl, dicyclononylmethyl and dicyclodecylmethyl, or endo-2-norbornyl, R$^{11}$ and R$^{15}$ are independently selected from hydrogen, halo, C$_1$-C$_6$ alkyl, C$_2$-C$_6$ alkenyl, C$_2$-C$_6$ alkynyl, heteroaryl, C$_1$-C$_6$ alkylthio, C$_1$-C$_6$ alkoxy, and C$_1$-C$_6$ alkylamino;

R$^{12}$ and R$^{13}$ are independently selected from hydrogen, hydroxyl, amino, mercapto, ureido, C$_1$-C$_6$ alkyl carbonylamino, hydroxy C$_1$-C$_6$ alkyl, and hydrazinyl; and R$^{14}$ is selected from hydrogen, C$_1$-C$_3$ alkoxycarbonyl, C$_1$-C$_3$ alkyl aminocarbonyl, hydroxy C$_1$-C$_3$ alkyl aminocarbonyl, di(C$_1$-C$_3$ alkyl) aminocarbonyl, C$_3$-C$_8$ cycloalkyl aminocarbonyl, C$_1$-C$_3$ alkylthio C$_1$-C$_3$ alkyl, C$_6$-C$_{10}$ arylthio C$_1$-C$_3$ alkyl, halo C$_1$-C$_3$ alkyl, hydrazinyl, amino C$_1$-C$_3$ alkyl, hydroxy C$_1$-C$_3$ alkyl, C$_3$-C$_6$ cycloalkylamino, hydroxylamino, and C$_2$-C$_3$ alkenyl, wherein the aryl portion is optionally substituted with one or more substituents selected from halo and C$_1$-C$_3$ alkoxy;

or a pharmaceutically acceptable salt thereof.

In an aspect, when R$^{11}$ is chloro and R$^{14}$ is hydrogen, R$^{10}$ is not dicyclopentylmethyl.

In an aspect, R$^{15}$ is hydrogen.

In certain aspects, Y is N.

In an aspect, R$^{12}$ and R$^{13}$ are both hydroxyl.

In certain aspects, R$^1$ is H or chloro.

In an aspect, R$^{14}$ is H.

In certain aspects, R$^{10}$ is dicyclobutylmethyl

In a particular aspect, the compound is:

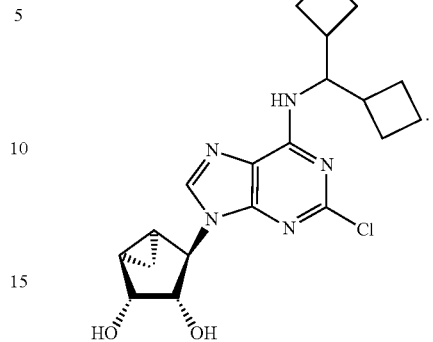

In certain aspects, R$^{14}$ is halo C$_1$-C$_3$ alkyl or hydroxy C$_1$-C$_3$ alkyl.

In certain particular aspects, the compound is selected from:

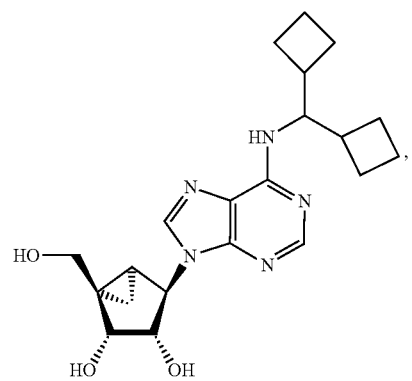

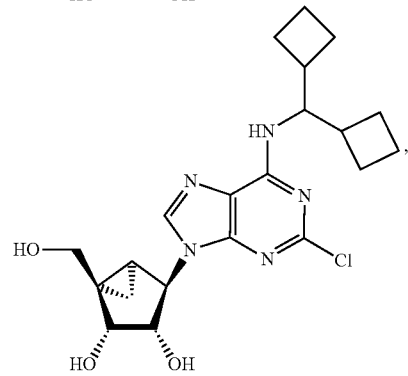

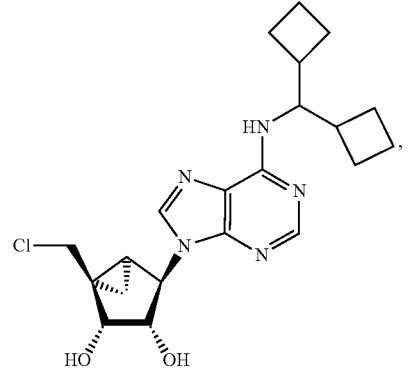

In certain aspects, $R^{14}$ is $C_1$-$C_3$ alkoxycarbonyl, $C_1$-$C_3$ alkyl aminocarbonyl, hydroxy $C_1$-$C_3$ alkyl aminocarbonyl, or $C_3$-$C_8$ cycloalkyl aminocarbonyl.

In certain particular aspects, the compound is:

In certain aspects, Y in the compound of formula (II) is CH.

In a particular aspect, the compound is:

In a further aspect, the invention provides a compound of formula (III):

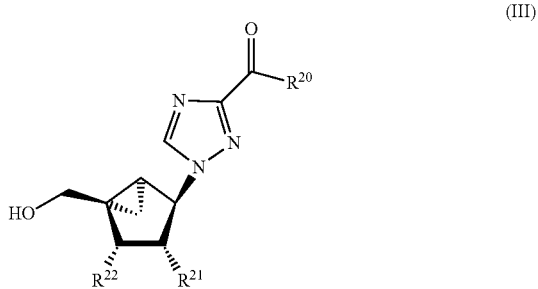

(III)

wherein $R^{20}$ is amino, $C_1$-$C_3$ alkoxy, $C_1$-$C_3$ alkylamino, hydroxy $C_1$-$C_3$ alkylamino, di($C_1$-$C_3$ alkyl)amino, or $C_3$-$C_5$ cycloalkylamino, and $R^{21}$ and $R^{22}$ are independently selected from hydrogen, hydroxyl, amino, mercapto, ureido, $C_1$-$C_6$ alkyl carbonylamino, hydroxy $C_1$-$C_6$ alkyl, and hydrazinyl, or a pharmaceutically acceptable salt thereof.

In an aspect, $R^{21}$ and $R^{22}$ are both hydroxyl.

In particular aspects, the compound is:

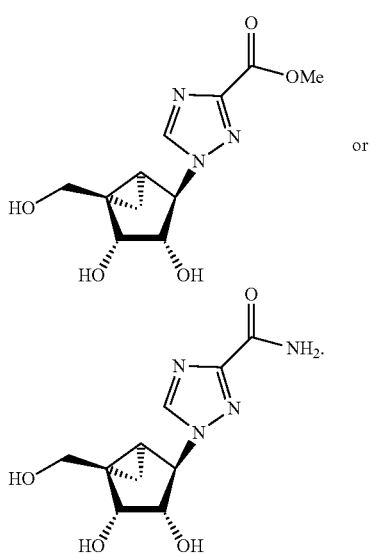

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkenyl," as used herein, means a $C_2$-$C_6$ alkenyl group containing one or more double bonds.

The term "cycloalkyl," as used herein, means a cyclic alkyl substituent containing from, for example, 4 to about 10 carbon atoms. Examples of such substituents include cyclobutyl, cyclopentyl, cyclohexyl, cycloheptyl, cyclooctyl, cyclononyl, cyclodecyl, and the like. The cyclic alkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable heterocyclyl groups include morpholine, piperidine, tetrahydrofuryl, oxetanyl, pyrrolidinyl, and the like. Suitable bicyclic heterocyclyl groups include monocyclic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. The term "heteroaryl" refers to a monocyclic or bicyclic 5- or 6-membered ring system as described herein, wherein the heteroaryl group is unsaturated and satisfies Hückel's rule. Non-limiting examples of suitable heteroaryl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, pyridazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl or heteroaryl group is optionally substituted with 1, 2, 3, 4, or 5 substituents as recited herein such as with alkyl groups such as methyl groups, ethyl groups, and the like, halo groups such as chloro, or hydroxyl groups, with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl or heteroaryl group, or with benzo groups, to form a group of, for example, benzofuran.

The term "alkylcarbonyl," as used herein, refers to an alkyl group linked to a carbonyl group and further linked to a molecule via the carbonyl group, e.g., alkyl-C(=O)—. The term "alkoxycarbonyl," as used herein, refers to an alkoxy group linked to a carbonyl group and further linked to a molecule via the carbonyl group, e.g., alkyl-O—C(=O)—. The term "aminocarbonyl," as used herein, refers to an amino group linked to a carbonyl group and further linked to a molecule via the carbonyl group, e.g., $H_2N$—C(=O)—. The term "alkyl aminocarbonyl," as used herein, refers to an alkylamino group linked to a carbonyl group and further linked to a molecule via the carbonyl group, e.g., alkyl-NH—C(=O)—. The term "dialkyl aminocarbonyl," as used herein, refers to a dialkylamino group linked to a carbonyl group and further linked to a molecule via the carbonyl group, e.g., (alkyl$^1$)(alkyl$^2$)-NH—C(=O)—. The term "hydroxyalkyl aminocarbonyl," as used herein, refers to a hydroxyalkylamino group linked to a carbonyl group and further linked to a molecule via the carbonyl group, e.g., HO-alkyl-NH—C(=O)—. The alkyl groups in dialkyl aminocarbonyl can be the same alkyk group or different alkyl groups. The term "alkylthio alkyl," as used herein, refers to an alkylthio group linked to a second alkyl group and further linked to a molecule via the second alkyl group, e.g., alkyl-S-alkyl-. The terms "alkylthio," "alkoxy," and "alkylamino," as used herein, refer to an alkyl group linked to a sulfur atom, oxygen atom, and nitrogen atom, respectively, and further linked to a molecule via the sulfur atom, oxygen atom, and nitrogen atom, e.g., alkyl-S—, alkyl-O—, and alkyl-NH—.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise $4n+2$ $\pi$ electrons, according to Hückel's Rule.

Whenever a range of the number of atoms in a structure is indicated (e.g., a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, PA, 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

In any of the above aspects, the compound or salt of formula (I) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, i.e., as mixtures of equal amounts of optical isomers, i.e., equal amounts of two enantiomers, or in the form of a single enantiomer. As used herein, "single enantiomer" is intended to include a compound that comprises more than 50% of a single enantiomer (i.e., enantiomeric excess up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (i.e., diastereomeric excess to 100% pure diastereomer).

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some aspects, the composition contains at least one active component and a suitable vehicle or carrier. It may also contain other components, such as an anti-irritant. The carrier can be a liquid, solid or semi-solid. In aspects, the composition is an aqueous solution. Alternatively, the composition can be a dispersion, emulsion, gel, lotion or cream vehicle for the various components. In one aspect, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In aspects of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Chemistry

Representative routes to the compounds of the invention are shown in Schemes 1-4.

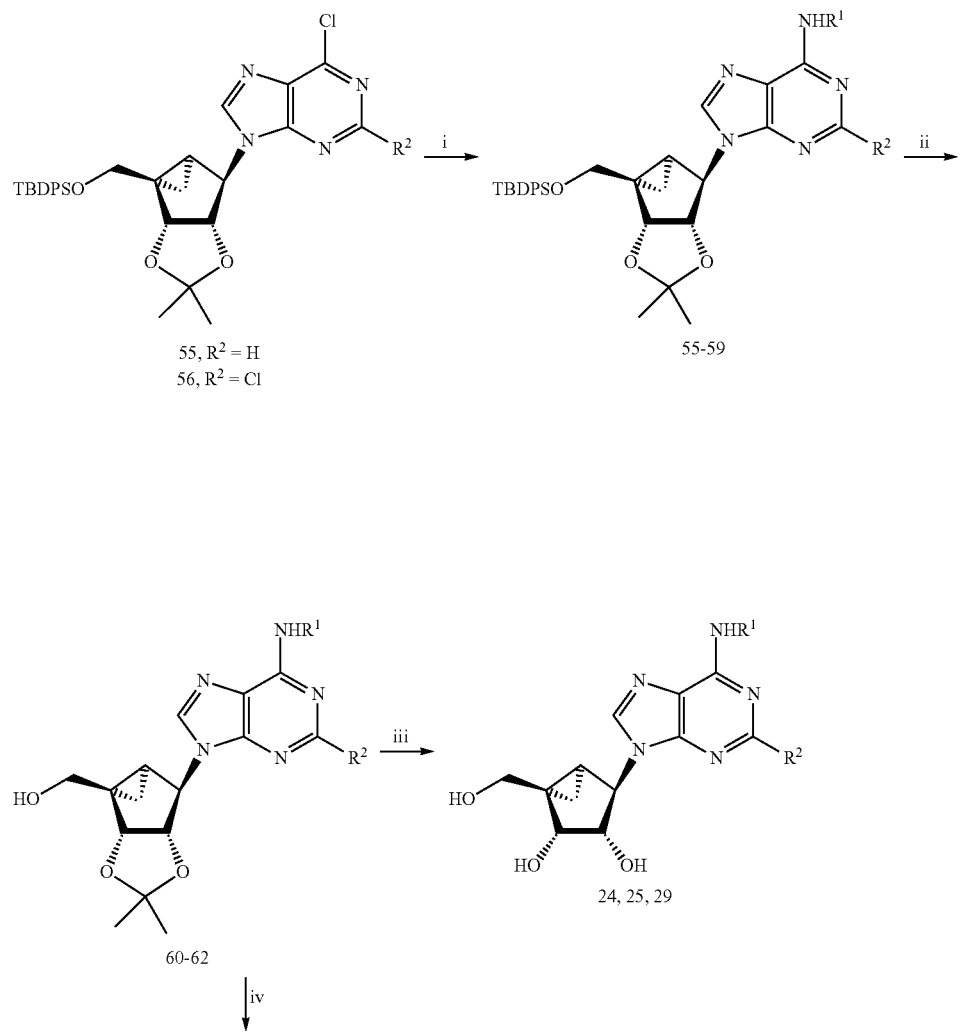

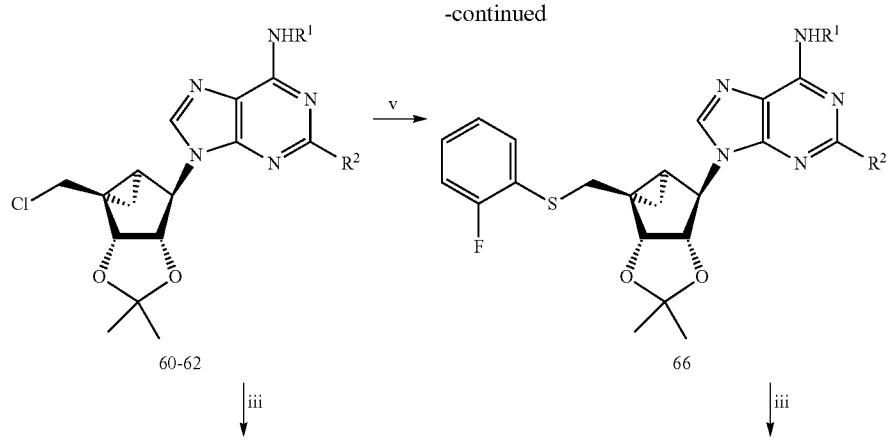
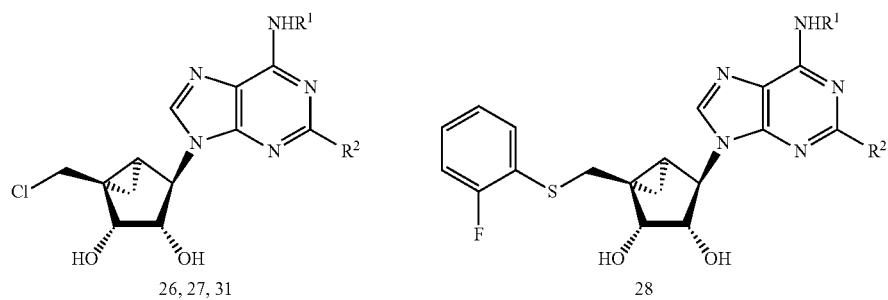
Reagents and Conditions:
I, R¹NH₂, DIPEA, 2-propanol, rt;
ii, TBAF, THF, rt;
iii, 10% TFA, MeOH, 70° C.;
iv, SOCl₂, pyridine, CH₃CN, -5° C.;
v, 2-F-PhSH, NaH, DMF, 0° C. -> rt.
Scheme 2: Synthesis of Ribose Analogs (compounds of formula (I))
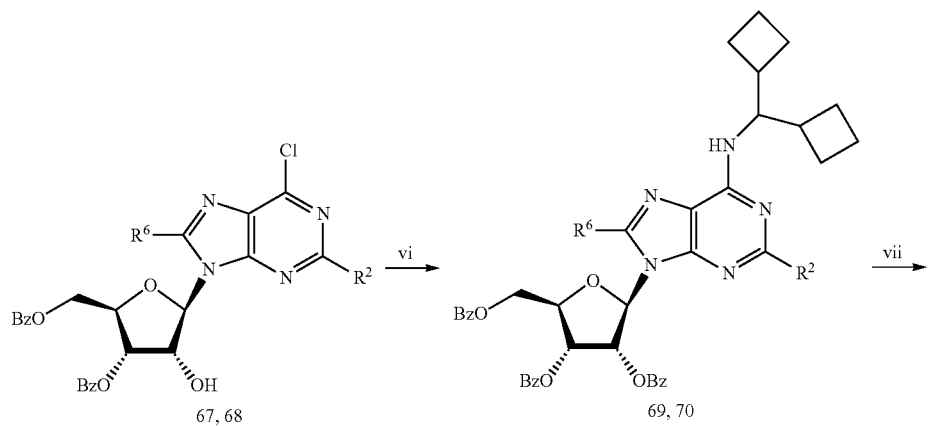

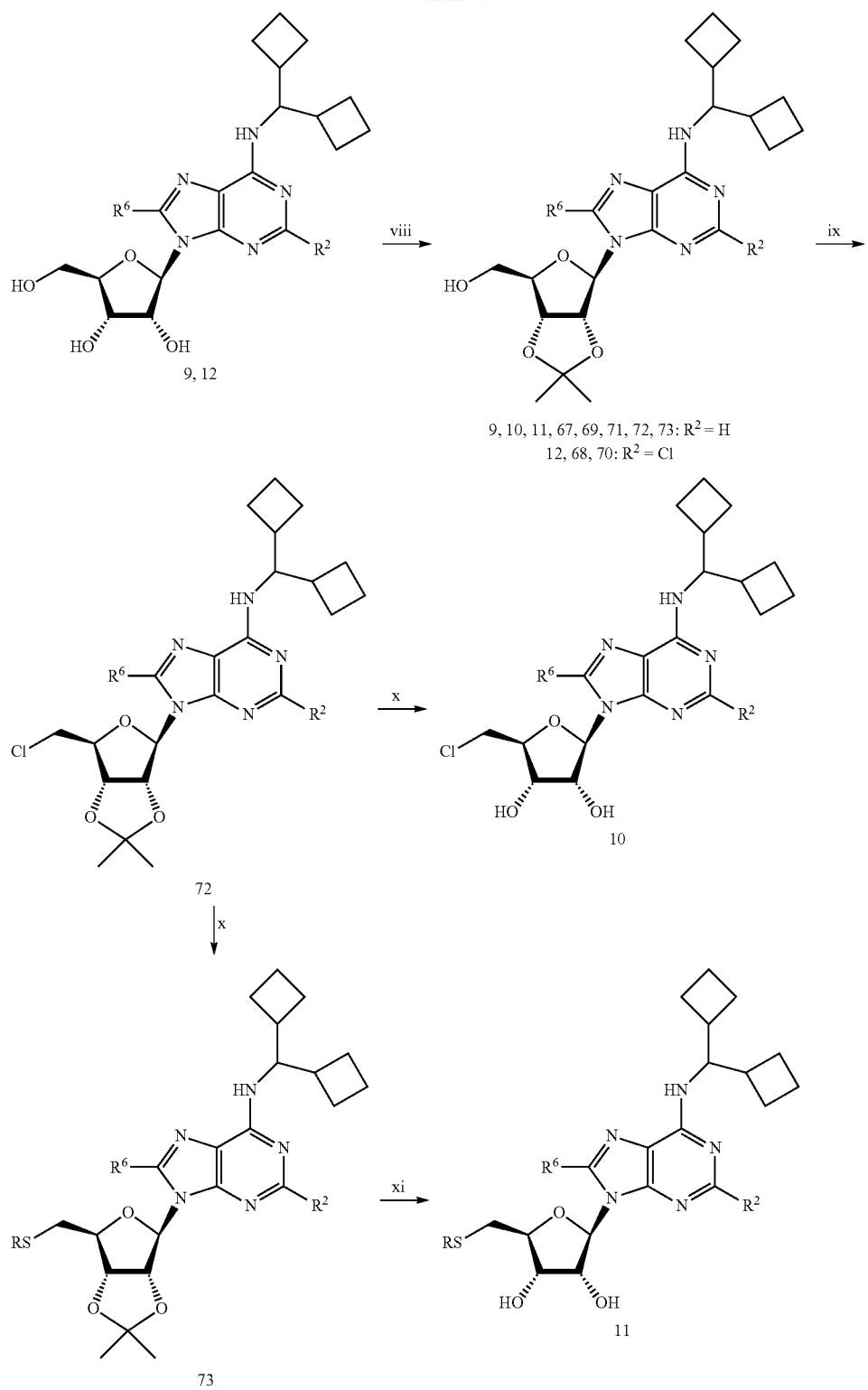
9, 10, 11, 67, 69, 71, 72, 73: R² = H
12, 68, 70: R² = Cl
Reagents and Conditions:
vi, dicyclobutylmethylamine, DIPEA, 2-propanol, rt;
vii, NH₃/MeOH, rt;
viii, 2-2,dimethoxypropane, p-TSA, acetone, rt;
iv, SOCl₂, pyridine, CH₃CN, 0° C. -> rt;
x, RSNa, DMF, rt;;
xi, 10% TFA, MeOH, 70° C.

Scheme 3: Synthesis of Synthesis of 5'-Carboxy Analogs (of formula (II))
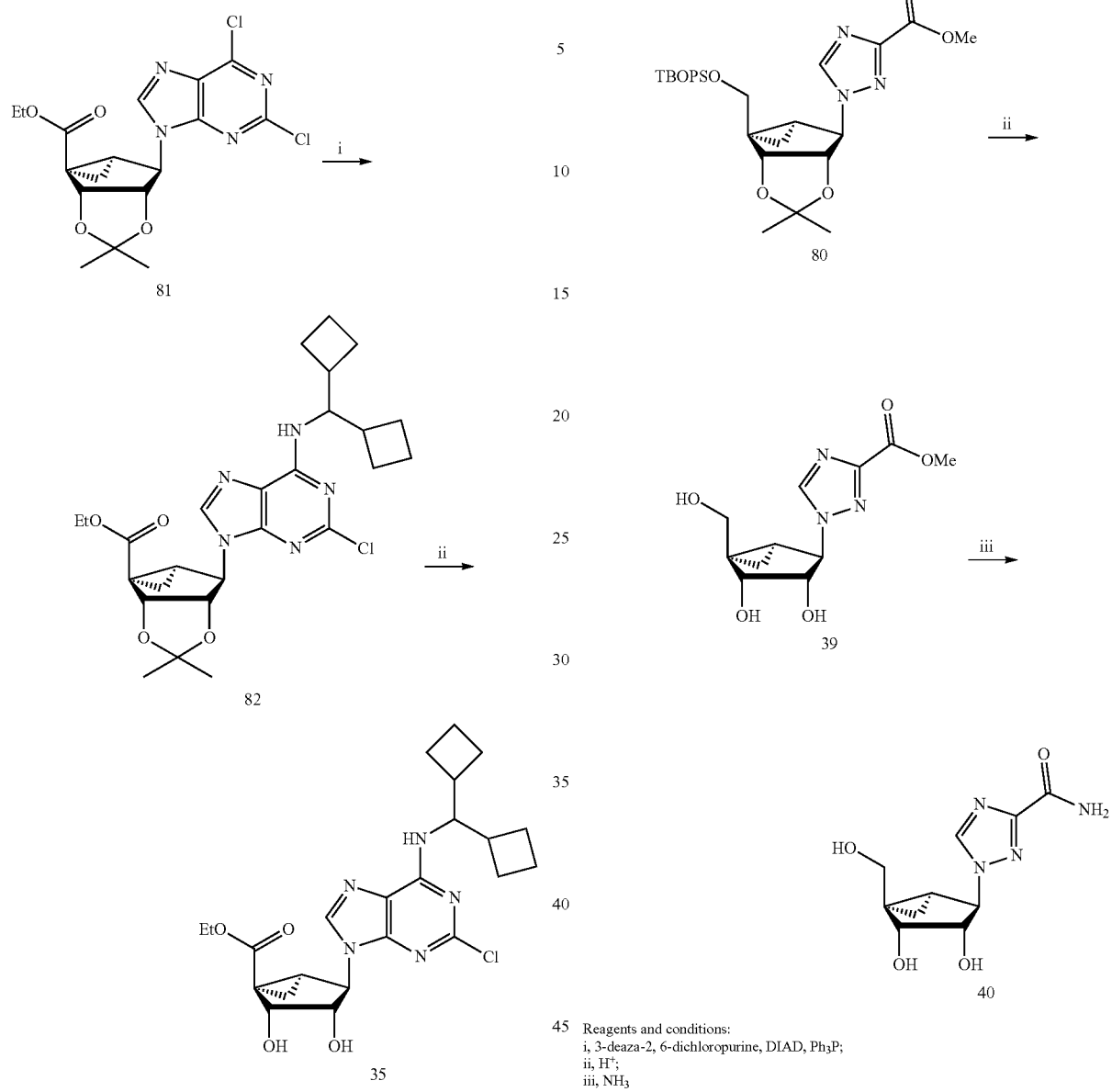
Reagents and conditions:
i, dicyclobutylmethylamine, base;
ii, H+
Scheme 4: Synthesis of Compounds of Formula (III)
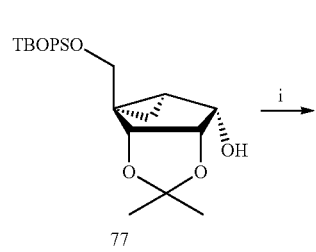
Reagents and conditions:
i, 3-deaza-2, 6-dichloropurine, DIAD, Ph₃P;
ii, H+;
iii, NH₃
Scheme 5
Synthesis of Dicyclobutylmethyl Analog of Compound of Formula (I)
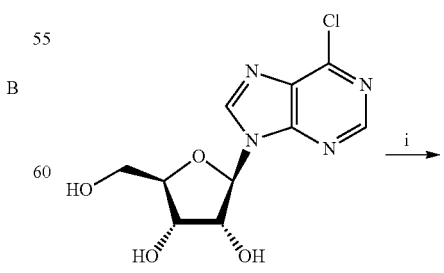

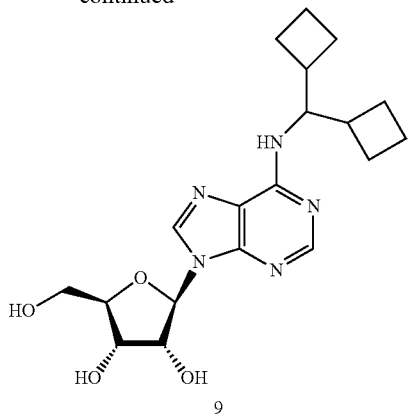

Reagents and conditions:
i, dicyclobutylmethylamine, DIPEA, 2 propanol, rt;

In certain aspects, the invention provides a method of inducing and/or maintaining a hypothermic and/or hypometabolic state for treatment of a mammal, comprising administering to the mammal an effective amount of a compound of any one of aspects of the invention or a pharmaceutically acceptable salt thereof. In certain of these aspects, the mammal has been afflicted with at least one of an anoxic, hypoxic, or hypoperfusion event. In certain preferred aspects, the anoxic, hypoxic, or hypoperfusion event is selected from birth injury, cardiac arrhythmia, heart attack, cardiac arrest, stroke, brain injury, trauma, and head injury.

In certain aspects, the invention provides a method of inducing and/or maintaining a hypothermic and/or hypometabolic state for treatment of a mammal, comprising administering to the mammal an effective amount of a compound of any one of aspects of the invention or a pharmaceutically acceptable salt thereof, wherein the mammal is, has been, or will be subjected to a surgical procedure. The compound can be administered before, during, or after the surgical procedure. In these aspects, the compound can be administered as a single dose or in multiple discrete doses at any time before, during, or after the surgical procedure. In other aspects, the compound can be administered continuously before, during, and after the surgical procedure. Non-limiting examples of suitable routes of administration in conjunction with surgical procedures include parenteral and/or intrathecal routes of administration.

In certain aspects, the invention provides a method of treating a disease or disorder in a mammal in need thereof, wherein the disease or disorder is selected from chronic pain, acute pain, diabetes, cardiac arrhythmia, myocardial infarction, depression and brain ischemia, comprising administering to the mammal an effective amount of a compound of any one of aspects of the invention or a pharmaceutically acceptable salt thereof.

In any of the above aspects, the compound or salt thereof can be administered parenterally or intrathecally to the mammal. In these aspects, the compound or salt thereof is preferably administered in the form of a pharmaceutical composition as described herein.

The compounds or salts thereof can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. For example, in aspects, the compounds or salts may be administered from about 1 mg/kg to about 1000 mg/kg, from about 1 mg/kg to about 500 mg/kg, from about 1 mg/kg to about 300 mg/kg, from about 1 mg/kg to about 100 mg/kg, from about 5 mg/kg to about 100 mg/kg, from about 1 mg/kg to about 50 mg/kg, from about 1 mg/kg to about 10 mg/kg, from about 120 mg/kg to about 280 mg/kg, from about 140 mg/kg to about 260 mg/kg, from about 150 mg/kg to about 250 mg/kg, or from about 160 mg/kg to about 240 mg/kg, of subject body weight per day, one or more times a day, to obtain the desired therapeutic effect.

The invention includes at least the following aspects.

Exemplary Aspects of Invention

1. A compound of formula (I):

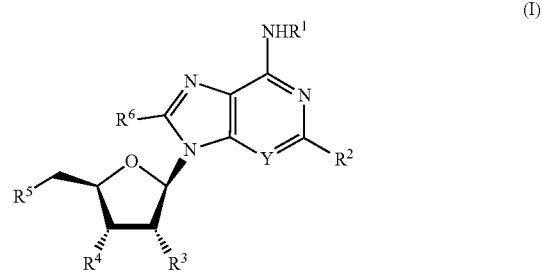

wherein Y is N or CH, $R^1$ is dicyclobutylmethyl, dicyclopentylmethyl, dicyclohexylmethyl, dicycloheptylmethyl, dicyclooctylmethyl, dicyclononylmethyl, or dicyclodecylmethyl, $R^2$ and $R^6$ are independently selected from hydrogen, halo, $C_1$-$C_6$ alkyl, $C_2$-$C_6$ alkenyl, $C_2$-$C_6$ alkynyl, heteroaryl, $C_1$-$C_6$ alkylthio, $C_1$-$C_6$ alkoxy, and $C_1$-$C_6$ alkylamino;

$R^3$ and $R^4$ are independently selected from hydrogen, hydroxyl, amino, mercapto, ureido, $C_1$-$C_6$ alkyl carbonylamino, hydroxy $C_1$-$C_6$ alkyl, and hydrazinyl; and $R^5$ is selected from hydrogen, hydroxyl, halo, $C_1$-$C_3$ alkyl aminocarbonyl, hydroxy $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;

or a pharmaceutically acceptable salt thereof.

2. The compound or salt of embodiment 1, wherein $R^6$ is hydrogen.

3. The compound or salt of embodiment 1 or 2, wherein Y is N.

4. The compound or salt of any one of embodiments 1-3, wherein $R^3$ and $R^4$ are both hydroxyl.

5. The compound or salt of any one of embodiments 1-4, wherein $R^5$ is selected from hydroxyl and halo.

6. The compound or salt of any one of embodiments 1-5, wherein $R^2$ is H or chloro.

7. The compound or salt of any one of embodiments 1-6, wherein the compound is:

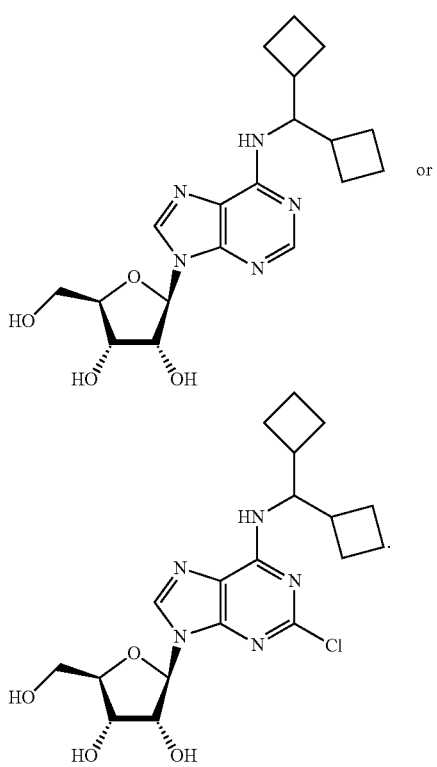

or

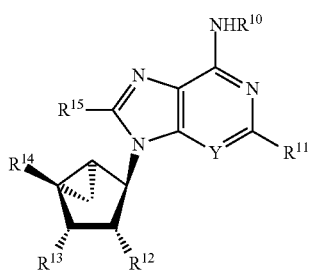

8. A pharmaceutical composition comprising a compound or salt of any one of embodiments 1-7 and a pharmaceutically acceptable carrier.

9. A compound of formula (II):

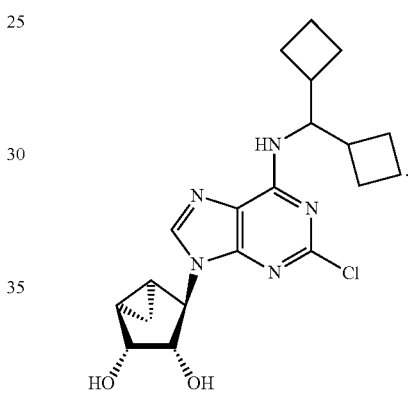
(II)

wherein Y is N or CH, $R^{10}$ is dicyclobutylmethyl, dicyclopentylmethyl, dicyclohexylmethyl, dicycloheptylmethyl, dicyclooctylmethyl, dicyclononylmethyl and dicyclodecylmethyl, or endo-2-norbornyl, $R^{11}$ and $R^{15}$ are independently selected from hydrogen, halo, $C_1$-$C_6$ alkyl, $C_2$-$C_6$ alkenyl, $C_2$-$C_6$ alkynyl, heteroaryl, $C_1$-$C_6$ alkylthio, $C_1$-$C_6$ alkoxy, and $C_1$-$C_6$ alkylamino;

$R^{12}$ and $R^{13}$ are independently selected from hydrogen, hydroxyl, amino, mercapto, ureido, $C_1$-$C_6$ alkyl carbonylamino, hydroxy $C_1$-$C_6$ alkyl, and hydrazinyl; and $R^{14}$ is selected from hydrogen, $C_1$-$C_3$ alkoxycarbonyl, $C_1$-$C_3$ alkyl aminocarbonyl, hydroxy $C_1$-$C_3$ alkyl aminocarbonyl, di($C_1$-$C_3$ alkyl) aminocarbonyl, $C_3$-$C_8$ cycloalkyl aminocarbonyl, $C_1$-$C_3$ alkylthio $C_1$-$C_3$ alkyl, $C_6$-$C_{10}$ arylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl, wherein the aryl portion is optionally substituted with one or more substituents selected from halo and $C_1$-$C_3$ alkoxy;

or a pharmaceutically acceptable salt thereof, with the proviso that when $R^{11}$ is chloro and $R^{14}$ is hydrogen, $R^{10}$ is not dicyclopentylmethyl.

10. The compound or salt of embodiment 9, wherein $R^{15}$ is hydrogen.

11. The compound or salt of embodiment 9 or 10, wherein Y is N.

12. The compound or salt of any one of embodiments 9-11, wherein $R^{12}$ and $R^{13}$ are both hydroxyl.

13. The compound or salt of any one of embodiments 9-12, wherein $R^{11}$ is H or chloro.

14. The compound or salt of any one of embodiments 9-13, wherein $R^{14}$ is H.

15. The compound or salt of embodiment 14, wherein the compound is:

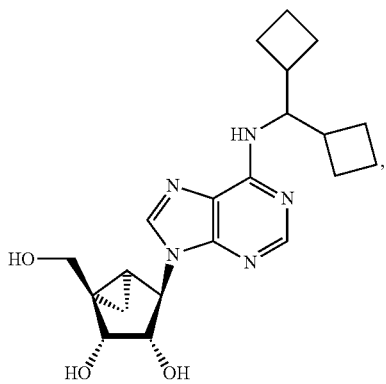

16. The compound or salt of any one of embodiments 9-13, wherein $R^{14}$ is halo $C_1$-$C_3$ alkyl or hydroxy $C_1$-$C_3$ alkyl.

17. The compound or salt of embodiment 16, wherein the compound is selected from:

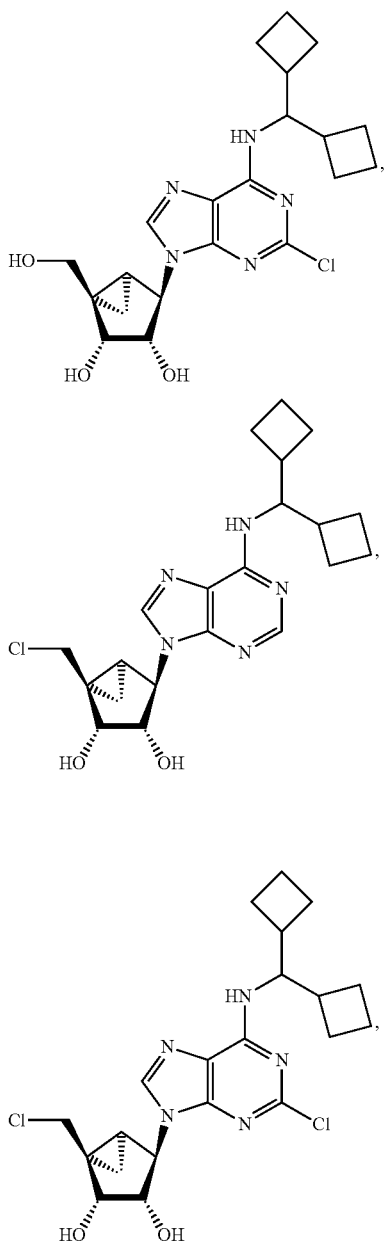
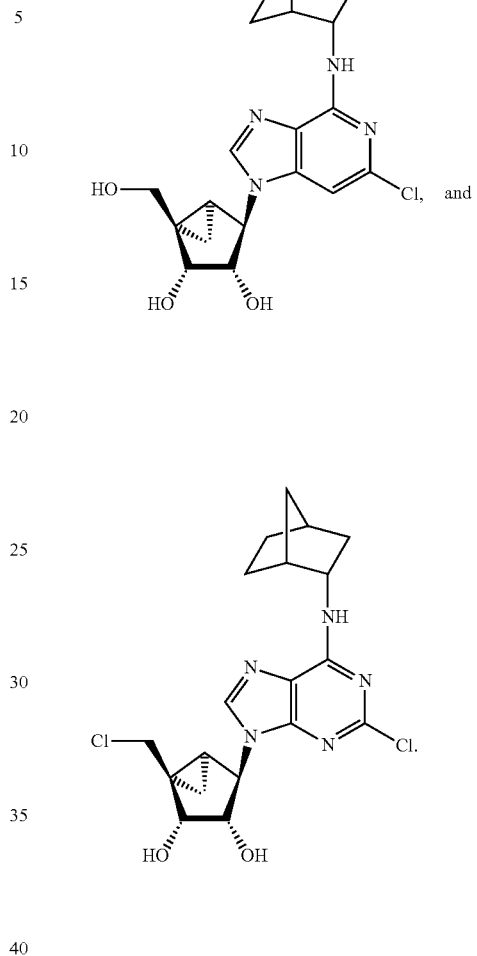
18. The compound or salt of any one of embodiments 9-13, wherein $R^{14}$ is $C_1$-$C_3$ alkoxycarbonyl, $C_1$-$C_3$ alkyl aminocarbonyl, hydroxy $C_1$-$C_3$ alkyl aminocarbonyl, or $C_3$-$C_8$ cycloalkyl aminocarbonyl.
19. The compound or salt of embodiment 18, wherein the compound is:
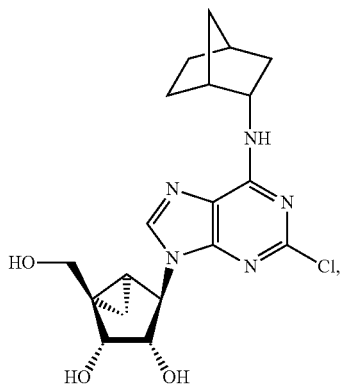
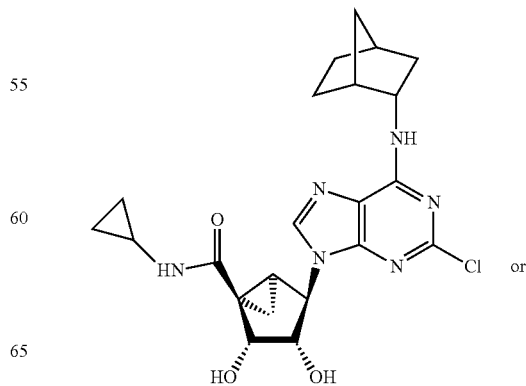

-continued

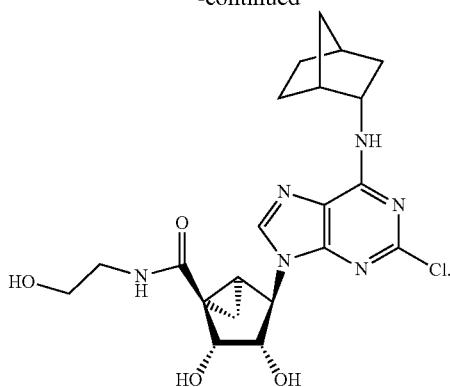

20. The compound or salt of embodiment 9 or 10, wherein Y is CH.

21. The compound of embodiment 20, wherein the compound is:

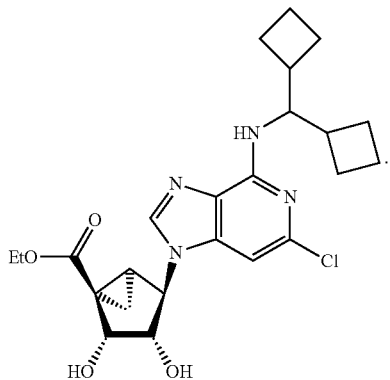

22. A pharmaceutical composition comprising a compound or salt of any one of embeds embodiments 9-21 and a pharmaceutically acceptable carrier.

23. A compound of formula (III):

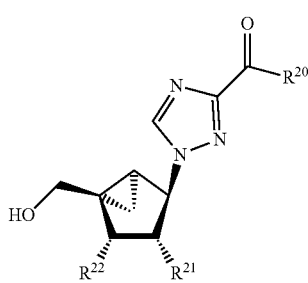

(III)

wherein $R^{20}$ is amino, $C_1$-$C_3$ alkoxy, $C_1$-$C_3$ alkylamino, hydroxy $C_1$-$C_3$ alkylamino, di($C_1$-$C_3$ alkyl)amino, or $C_3$-$C_8$ cycloalkylamino, and $R^{21}$ and $R^{22}$ are independently selected from hydrogen, hydroxyl, amino, mercapto, ureido, $C_1$-$C_6$ alkyl carbonylamino, hydroxy $C_1$-$C_6$ alkyl, and hydrazinyl, or a pharmaceutically acceptable salt thereof.

24. The compound or salt of embodiment 23, wherein $R^{21}$ and $R^{22}$ are both hydroxyl.

25. The compound or salt of embodiment 23 or 24, wherein the compound is:

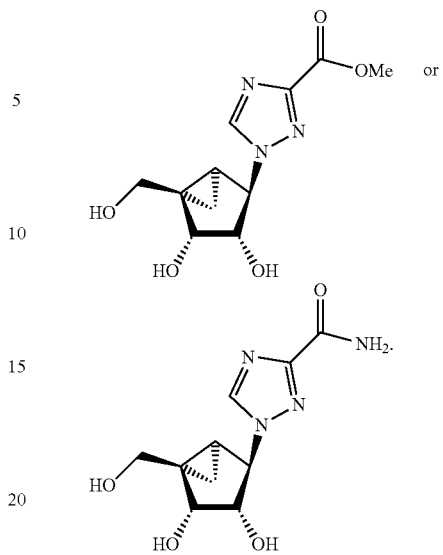

26. A pharmaceutical composition comprising a compound or salt of any one of embodiments 23-25 and a pharmaceutically acceptable carrier.

27. A method of inducing and/or maintaining a hypothermic and/or hypometabolic state for treatment of a mammal, comprising administering to the mammal an effective amount of a compound of any one of embodiments 1-7, 9-21, or 23-25.

28. The method of embodiment 27, wherein the mammal has been afflicted with at least one of an anoxic, hypoxic, or hypoperfusion event.

29. The method of embodiment 28, wherein the anoxic, hypoxic, or hypoperfusion event is selected from birth injury, cardiac arrhythmia, heart attack, cardiac arrest, stroke, brain injury, trauma, and head injury.

30. A method of inducing and/or maintaining a hypothermic and/or hypometabolic state in a mammal, comprising administering to the mammal an effective amount of a compound of any one of embodiments 1-7, 9-21, or 23-25, wherein the mammal is subjected to a surgical procedure.

31. The method of embodiment 30, wherein the compound is administered before, during, or after the surgical procedure.

32. A method of treating a disease or disorder in a mammal in need thereof, wherein the disease or disorder is selected from chronic pain, acute pain, diabetes, cardiac arrhythmia, myocardial infarction, depression and brain ischemia, comprising administering to the mammal an effective amount of a compound of any one of embodiments 1-7, 9-21, or 23-25.

33. The method of any one of embodiments 27-32, wherein the compound is administered intrathecally, orally, or parenterally.

The following examples further illustrate the invention but, of course, should not be construed as in any way limiting its scope.

Materials and Instrumentation

All reagents and solvents were purchased from Sigma-Aldrich (St. Louis, MO). $^1$H NMR spectra were obtained with a Bruker 400 spectrometer using CDCl$_3$, CD$_3$OD and DMSO as solvents. Chemical shifts are expressed in δ values (ppm) with tetramethylsilane (δ 0.00) for CDCl$_3$ and water (δ 3.30) for CD$_3$OD. NMR spectra were collected with a Bruker AV spectrometer equipped with a z-gradient [$^1$H, $^{13}$C, $^{15}$N]-cryoprobe. TLC analysis was carried out on glass sheets precoated with silica gel F254 (0.2 mm) from Aldrich. The purity of final nucleoside derivatives was checked using a Hewlett-Packard 1100 HPLC equipped with a Zorbax SB-Aq 5 μm analytical column (50×4.6 mm; Agilent Technologies Inc., Palo Alto, CA). Mobile phase: linear gradient solvent system, 5 mM TBAP (tetrabutylammonium dihydrogen phosphate)-CH$_3$CN from 80:20 to 0:100 in 13 min; the flow rate was 0.5 mL/min. Peaks were detected by UV absorption with a diode array detector at 230, 254, and 280 nm. All derivatives tested for biological activity showed >95% purity by HPLC analysis (detection at 254 nm). Low-resolution mass spectrometry was performed with a JEOL SX102 spectrometer with 6-kV Xe atoms following desorption from a glycerol matrix or on an Agilent LC/MS 1100 MSD, with a Waters (Milford, MA) Atlantis C18 column. High resolution mass spectroscopic (HRMS) measurements were performed on a proteomics optimized Q-TOF-2 (Micromass-Waters) using external calibration with polyalanine, unless noted. Observed mass accuracies are those expected based on known performance of the instrument as well as trends in masses of standard compounds observed at intervals during the series of measurements. Reported masses are observed masses uncorrected for this time-dependent drift in mass accuracy. All of the reagents were purchased from Sigma-Aldrich (St. Louis, MO), Small Molecules, Inc. (Hoboken, NJ), Anichem (North Brunswick, NJ), PharmaBlock, Inc. (Sunnyvale, CA), Frontier Scientific (Logan, UT) and Tractus (Perrineville, NJ).

Abbreviations:

AR, adenosine receptor; HEK 293, human embryonic kidney 293; DAT, the dopamine transporter; DMF, dimethylformamide; DIPEA, diisopropylethylamine; GPCR, G protein-coupled receptor; HRMS, high resolution mass spectrometry; MD, molecular dynamics; NET, the norepinephrine transporter; PDSP, NIMH Psychoactive Drug Screening Program; RMSD, root-mean-square deviation; SAR, structure activity relationship; SERT, the serotonin transporter; Tb, body temperature; TBAF, tetrabutylammonium fluoride; TBAP, tetrabutylammonium dihydrogenphosphate; TFA, trifluoroacetic acid; THF, tetrahydrofuran; TM, transmembrane; TSPO, the translocator protein.

Example 1

This example demonstrates a method of preparing compounds in accordance with an aspect of the invention.

(2R,3R,4R,5R)-2-(6-((Dicyclobutylmethyl)amino)-9H-purin-9-yl)-5-(hydroxymethyl)tetrahydrofuran-3,4-diol (9)

Saturated methanolic ammonia solution (25 mL) was added into the compound (425 mg, 0.60 mmol) and the solution stirred for overnight at temperature in a sealed tube. Solvent was evaporated and the residue was purified on flash silica gel column chromatography (CH$_2$Cl$_2$:MeOH=25:1) to give the compound 9 (220 mg, 93%) as colorless powder. $^1$H NMR (CD$_3$OD, 400 MHz) δ 8.28 (s, 1H), 8.20 (s, 1H), 5.97 (d, J=6.4 Hz, 1H), 4.77 (t, J=5.6 Hz, 1H), 4.41 (t, J=7.2 Hz, 1H), 4.34 (d, J=4.8 Hz, 1H), 4.19 (d, J=6.0 Hz, 1H), 3.92 (d, J$_1$=2.4 Hz, J$_2$=12.4 Hz, 1H), 3.78 (d, J$_1$=2.4 Hz, J$_2$=12.4 Hz, 1H), 2.55-2.51 (m, 2H), 2.02-1.83 (m, 10H), 1.79-1.75 (m, 2H). HRMS calc. C$_{19}$H$_{28}$N$_5$O$_4$ (M+H)$^+$: 390.2141; found 390.2144.

(2S,3S,4R,5R)-2-(Chloromethyl)-5-(6-((dicyclobutylmethyl)amino)-9H-purin-9-yl)tetrahydrofuran-3,4-diol (10)

Compound 10 (89%) was prepared from compound 72 following the same method as for compound 24. $^1$H NMR (CD$_3$OD, 400 MHz) δ 8.27 (s, 1H), 8.24 (s, 1H), 6.05 (d, J=5.2 Hz, 1H), 4.79 (d, J=5.2 Hz, 1H), 4.41-4.39 (m, 2H), 4.31-4.27 (d, J$_1$=4.8 Hz, J$_2$=5.2 Hz, 1H), 3.97 (d, J$_1$=5.2 Hz, J$_2$=6.8 Hz, 1H), 3.87 (d, J$_1$=5.2 Hz, J$_2$=6.8 Hz, 1H), 2.57-2.50 (m, 2H), 2.01-1.83 (m, 10H), 1.79-1.75 (m, 2H). HRMS calc. C$_{19}$H$_{27}$N$_5$O$_4$Cl (M+H)$^+$: 408.1802; found 408.1800.

(2R,3R,4S,5S)-2-(6-((Dicyclobutylmethyl)amino)-9H-purin-9-yl)-5-((ethylthio)methyl)tetrahydrofuran-3,4-diol (11)

Compound 11 (91%) was prepared from compound 73 following the same method as for compound 24. $^1$H NMR (CD$_3$OD, 400 MHz) δ 8.30 (s, 1H), 8.23 (s, 1H), 6.02 (d, J=5.2 Hz, 1H), 4.78 (t, J=6.0 Hz, 1H), 4.39-4.33 (m, 2H), 4.24-4.21 (m, 1H), 3.01 (d, J$_1$=5.6 Hz, J$_2$=8.8 Hz, 1H), 2.93 (d, J$_1$=5.6 Hz, J$_2$=8.8 Hz, 1H), 2.63-2.48 (m, 4H), 2.01-1.83 (m, 10H), 1.76-1.75 (m, 2H), 1.22 (t, J=7.6 Hz, 3H). HRMS calc. C$_{21}$H$_{32}$N$_5$O$_3$S (M+H)$^+$: 434.2226; found 434.2232.

(2R,3R,4R,5R)-2-(2-Chloro-6-((dicyclobutylmethyl)amino)-9H-purin-9-yl)-5-(hydroxymethyl)tetrahydrofuran-3,4-diol (12)

Compound 12 (91%) was prepared from compound 70 following the same method as for compound 9. $^1$H NMR (CD$_3$OD, 400 MHz) δ 8.25 (s, 1H), 5.92 (d, J=6.0 Hz, 1H), 4.70 (t, J=5.2 Hz, 1H), 4.40-4.32 (m, 2H), 4.17 (d, J=6.8 Hz, 1H), 3.92 (d, J$_1$=2.4 Hz, J$_2$=10.0 Hz, 1H), 3.78 (d, J$_1$=2.4 Hz, J$_2$=10.0 Hz, 1H), 2.55-2.47 (m, 2H), 2.01-1.84 (m, 10H), 1.77-1.76 (m, 2H). HRMS calc. C$_{19}$H$_{27}$N$_5$O$_4$Cl (M+H)$^+$: 424.1752; found 424.1750.

(1R,2R,3S,4R,5S)-4-(6-((Dicyclobutylmethyl)amino)-9H-purin-9-yl)-1-(hydroxymethyl)bicyclo[3.1.0]hexane-2,3-diol (24)

A solution of compound 60 (30 mg, 0.02 mmol) in methanol (3 mL) and 10% TFA in water (3 mL) was heated at 70° C. for 6 hrs. Solvent was evaporated under vacuum and the residue was purified on flash silica gel silica chromatography (CH$_2$Cl$_2$:MeOH=25:1) to give the compound 24 (23 mg, 86%) as a syrup. $^1$H NMR (CD$_3$OD, 400 MHz) δ 8.47 (s, 1H), 8.22 (s, 1H), 4.82 (d, J=6.4 Hz, 1H), 4.40 (t, J=6.8 Hz, 1H), 4.31 (d, J=11.6 Hz, 1H), 3.91 (d, J=6.4 Hz, 1H), 3.33 (d, J=11.6 Hz, 1H), 2.54-2.50 (m, 2H), 1.98-1.83 (m, 10H), 1.76-1.75 (m, 2H), 1.68-1.65 (m, 1H), 1.54 (t, J=5.2 Hz, 1H), 0.78-0.75 (m, 1H). HRMS calc. C$_{21}$H$_{30}$N$_5$O$_3$ (M+H)$^+$: 400.2349; found 400.2356.

(1R,2R,3S,4R,5S)-4-(2-Chloro-6-((dicyclobutylmethyl)amino)-9H-purin-9-yl)-1-(hydroxymethyl)bicyclo[3.1.0]hexane-2,3-diol (25)

Compound 25 (87%) was prepared from compound 61 following the same method for compound 24. $^1$H NMR (CD$_3$OD, 400 MHz) δ 8.44 (s, 1H), 4.81 (s, 1H), 4.79 (d, J=6.8 Hz, 1H), 4.37 (d, J=8.0 Hz, 1H), 4.29 (d, J=11.6 Hz, 1H), 3.90 (d, J=6.4 Hz, 1H), 2.53-2.47 (m, 2H), 1.99-1.88 (m, 10H), 1.84-1.82 (m, 2H), 1.65-1.62 (m, 1H), 1.56 (d, J=4.8 Hz, 1H), 0.78-0.75 (m, 1H). HRMS calc. $C_{21}H_{29}N_5O_3Cl$ (M+H)$^+$: 434.1959; found 434.1964.

(1S,2R,3S,4R,5S)-1-(Chloromethyl)-4-(6-((dicyclobutylmethyl)amino)-9H-purin-9-yl)bicyclo[3.1.0]hexane-2,3-diol (26)

Compound 26 (88%) was prepared from compound 63 following the same method for compound 24. $^1$H NMR (CD$_3$OD, 400 MHz) δ 8.36 (s, 1H), 8.25 (s, 1H), 4.83 (d, J=6.0 Hz, 1H), 4.40 (t, J=7.2 Hz, 1H), 4.33 (d, J=11.6 Hz, 1H), 4.01 (d, J=6.4 Hz, 1H), 3.65 (d, J=11.6 Hz, 1H), 2.54-2.51 (m, 2H), 1.99-1.83 (m, 10H), 1.79-1.75 (m, 4H), 0.99-0.95 (m, 1H). HRMS calc. $C_{21}H_{29}N_5O_2Cl$ (M+H)$^+$: 418.2010; found 418.2016.

(1S,2R,3S,4R,5S)-4-(2-Chloro-6-((dicyclobutylmethyl)amino)-9H-purin-9-yl)-1-(chloromethyl)bicyclo[3.1.0]hexane-2,3-diol (27)

Compound 27 (89%) was prepared from compound 64 following the same procedure as for compound 24. $^1$H NMR (CD$_3$OD, 400 MHz) δ 8.29 (s, 1H), 4.83-4.80 (m, 2H), 4.38 (t, J=8.0 Hz, 1H), 4.31 (d, J=11.6 Hz, 1H), 3.99 (d, J=6.8 Hz, 1H), 3.69 (d, J=11.6 Hz, 1H), 2.53-2.47 (m, 2H), 1.99-1.88 (m, 10H), 1.84-1.74 (m, 4H), 0.99-0.95 (m, 1H). HRMS calc. $C_{21}H_{28}N_5O_2Cl_2$ (M+H)$^+$: 452.1620; found 452.1624.

(1S,2R,3S,4R,5S)-4-(2-Chloro-6-((dicyclobutylmethyl)amino)-9H-purin-9-yl)-1-(((2-fluorophenyl)thio)methyl)bicyclo[3.1.0]hexane-2,3-diol (28)

Compound 28 (90%) was prepared from compound 66 following the same procedure as for compound 24. $^1$H NMR (CD$_3$OD, 400 MHz) δ 8.13 (s, 1H), 7.49-7.45 (m, 1H), 7.20-7.15 (m, 1H), 7.07-7.02 (m, 2H), 4.84 (d, J=6.0 Hz, 1H), 4.71 (s, 1H), 4.38 (t, J=7.6 Hz, 1H), 4.05 (d, J=6.8 Hz, 1H), 3.69 (d, J=13.6 Hz, 11H), 3.31 (d, J=13.6 Hz, 1H), 2.54-2.48 (m, 2H), 2.02-1.89 (m, 10H), 1.84-1.77 (m, 2H), 1.59-1.54 (m, 2H), 0.91-0.87 (m, 1H). HRMS calc. $C_{27}H_{32}N_5O_2ClSF$ (M+H)$^+$: 544.1949; found 544.1951.

(1R,2R,3S,4R,5S)-4-(6-(((1R,2S,4S)-Bicyclo[2.2.1]heptan-2-yl)amino)-2-chloro-9H-purin-9-yl)-1-(hydroxymethyl)bicyclo[3.1.0]hexane-2,3-diol (29)

Compound 29 (84%) was prepared from compound 62 following the same method for compound 24. $^1$H NMR (CD$_3$OD, 400 MHz) δ 8.44 (s, 1H), 4.80 (s, 1H), 4.77 (d, J=6.8 Hz, 1H), 4.29 (d, J=11.6 Hz, 1H), 4.30 (br s, 1H), 3.88 (d, J=6.8 Hz, 1H), 3.38 (d, J=11.6 Hz, 1H), 2.35-2.34 (m, 2H), 1.93-1.87 (m, 1H), 1.64-1.53 (m, 5H), 1.49-1.34 (m, 2H), 1.27-1.21 (m, 2H), 0.78-0.74 (m, 1H). HRMS calc. $C_{19}H_{25}N_5O_3Cl$ (M+H)$^+$: 406.1646; found 406.1647.

(1S,2R,3S,4R,5S)-4-(6-(((1R,2S,4S)-Bicyclo[2.2.1]heptan-2-yl)amino)-2-chloro-9H-purin-9-yl)-1-(chloromethyl)bicyclo[3.1.0]hexane-2,3-diol (31)

Compound 31 (93%) was prepared from compound 65 following the same procedure as for compound 24. $^1$H NMR (CD$_3$OD, 400 MHz) δ 8.28 (s, 1H), 4.81-4.79 (m, 2H), 4.31 (d, J=11.6 Hz, 11H), 4.03 (br s, 11H), 3.97 (d, J=6.8 Hz, 11H), 3.68 (d, J=11.6 Hz, 11H), 2.38-2.32 (m, 2H), 1.92-1.87 (m, 1H), 1.82-1.79 (m, 1H), 1.75 (t, J=4.8 Hz, 1H), 1.61-1.55 (m, 3H), 1.48-1.34 (m, 2H), 1.30-1.23 (m, 2H), 0.98-0.96 (m, 1H). HRMS calc. $C_{19}H_{24}N_5O_2Cl_2$ (M+H)$^+$: 424.1307; found 424.1314.

9-((3aR,3bR,4aS,5R,5aS)-3b-(((tert-Butyldiphenylsilyl)oxy)methyl)-2,2-dimethylhexahydrocyclopropa[3,4]cyclopenta[1,2-d][1,3]dioxol-5-yl)-N-(dicyclobutylmethyl)-9H-purin-6-amine (57)

Dicyclobutylmethylamine (302 mg, 2.17 mmol) and DIPEA (0.75 mL, 4.37 mmol) were added to a solution of compound 55 (250 mg, 0.43 mmol) in 2-propanol and the solution heated at 75° C. for overnight. Solvent was evaporated under vacuum and the residue was purified on flash silica gel column chromatography (hexane:ethyl acetate=3:1) to give the compound 57 (267 mg, 91%) as a colorless syrup. $^1$H NMR (CD$_3$OD, 400 MHz) δ 8.36 (s, 11H), 8.19 (s, 11H), 7.67-7.644 (m, 4H), 7.44-7.33 (m, 6H), 5.40 (d, J=7.2 Hz, 11H), 5.04 (s, 11H), 4.72 (d, J=6.8 Hz, 11H), 4.40 (t, J=7.2 Hz, 11H), 4.23 (d, J=10.8 Hz, 11H), (d, J=10.8 Hz, 1H), 2.54-2.50 (m, 2H), 1.99-1.88 (m, 10H), 1.76-1.75 (m, 2H), 1.66-1.65 (m, 1H), 1.51 (s, 3H), 1.25 (s, 3H), 1.16 (t, J=4.8 Hz, 1H), 1.10 (s, 9H), 0.92-0.88 (m, 1H). HRMS calc. $C_{40}H_{52}N_5O_3Si$ (M+H)$^+$: 678.3839; found 678.3832.

9-((3aR,3bR,4aS,5R,5aS)-3b-(((tert-Butyldiphenylsilyl)oxy)methyl)-2,2-dimethylhexahydrocyclopropa[3,4]cyclopenta[1,2-d][1,3]dioxol-5-yl)-2-chloro-N-(dicyclobutylmethyl)-9H-purin-6-amine (58)

Compound 58 (87%) was prepared from compound 56 following the same method for compound 57. $^1$H NMR (CD$_3$OD, 400 MHz) δ 8.27 (s, 1H), 7.66 (d, J=6.8 Hz, 4H), 7.44-7.31 (m, 6H), 5.35 (d, J=7.2 Hz, 1H), 4.95 (s, 1H), 4.71 (d, J=7.2 Hz, 1H), 4.39 (t, J=8.0 Hz, 1H), 4.23 (d, J=6.4 Hz, 1H), 3.76 (d, J=10.8 Hz, 1H), 2.54-2.50 (m, 2H), 2.01-1.89 (m, 10H), 1.83-1.76 (m, 2H), 1.63-1.60 (m, 1H), 1.52 (s, 3H), 1.26 (s, 3H), 1.14-1.11 (m, 1H), 1.08 (s, 9H), 0.98-0.93 (m, 1H). HRMS calc. $C_{40}H_{51}N_5O_3SiCl$ (M+H)$^+$: 712.3450; found 712.3445.

N-((1R,2S,4S)-Bicyclo[2.2.1]heptan-2-yl)-9-((3aR,3bR,4aS,5R,5aS)-3b-(((tert-butyldiphenylsilyl)oxy)methyl)-2,2-dimethylhexahydrocyclopropa[3,4]cyclopenta[1,2-d][1,3]dioxol-5-yl)-2-chloro-9H-purin-6-amine (59)

(1R, 2S, 4S)-Bicyclo[2.2.1]nonane (306 mg, 2.75 mmol) and triethylamine (0.76 mL, 5.51 mmol) were added to a solution of compound 56 (336 mg, 0.55 mmol) in methanol and the solution stirred at room temperature for overnight. Solvent was evaporated under vacuum and the residue was purified on flash silica gel column chromatography (hexane:ethyl acetate=4:1) to give the compound 59 (319 mg, 82%) as a colorless syrup. 1H NMR (CD$_3$OD, 400 MHz) δ 8.26 (s, 1H), 7.66-7.64 (m, 4H), 7.43-7.32 (m, 6H), 5.34 (d, J=6.8 Hz, 1H), 4.95 (s, 1H), 4.69 (d, J=7.2 Hz, 1H), 4.22 (d, J=6.8 Hz, 1H), 4.03 (br s, 1H), 3.76 (d, J=6.8 Hz, 1H), 2.36-2.34 (m, 2H), 1.94-1.87 (m, 1H), 1.62-1.59 (m, 4H), 1.52 (s, 3H), 1.48-1.36 (m, 2H), 1.29-1.24 (m, 5H), 1.12 (t, J=5.2 Hz, 1H), 1.09 (s, 9H), 0.98-0.94 (m, 1H). HRMS calc. $C_{38}H_{47}N_5O_3SiCl$ (M+H)$^+$: 684.3137; found 684.3143.

((3aR,3bR,4aS,5R,5aS)-5-(6-((Dicyclobutylmethyl)amino)-9H-purin-9-yl)-2,2-dimethyltetrahydrocyclopropa[3,4]cyclopenta[1,2-d][1,3]dioxol-3b(3aH)-yl)methanol (60)

TBAF (0.6 mL, 1M solution in THF) was added to a solution of compound 57 (267 mg, 0.39 mmol) in THF and the solution stirred for 1 h at room temperature. Solvent was evaporated and the residue was purified on silica gel column chromatography ($CH_2Cl_2$:MeOH=30:1) to give the compound 60 (161 mg, 93%) as a colorless syrup. $^1$H NMR ($CD_3OD$, 400 MHz) δ 8.29 (s, 1H), 8.21 (s, 1H), 5.43 (d, J=7.2 Hz, 1H), 5.03 (s, 1H), 4.69 (d, J=7.2 Hz, 1H), 4.40 (t, J=6.4 Hz, 1H), 4.11 (d, J=10.8 Hz, 1H), 3.46 (d, J=10.8 Hz, 1H), 2.55-2.51 (m, 2H), 1.98-1.82 (m, 10H), 1.79-1.76 (m, 3H), 1.53 (s, 3H), 1.25 (s, 3H), 1.19 (t, J=5.2 Hz, 1H), 1.00-0.96 (m, 1H). HRMS calc. $C_{24}H_{34}N_5O_3$ (M+H)$^+$: 440.2662; found 440.2662.

((3aR,3bR,4aS,5R,5aS)-5-(2-Chloro-6-((dicyclobutylmethyl)amino)-9H-purin-9-yl)-2,2-dimethyl-tetrahydrocyclopropa[3,4]cyclopenta[1,2-d][1,3]dioxol-3b(3aH)-yl)methanol (61)

Compound 61 (89%) was prepared from compound 58 following the same method for compound 60. $^1$H NMR ($CD_3OD$, 400 MHz) δ 8.22 (s, 1H), 5.39 (d, J=7.2 Hz, 1H), 4.95 (s, 1H), 4.71 (d, J=6.8 Hz, 1H), 4.38 (t, J=8.0 Hz, 1H), 4.01 (d, J=11.6 Hz, 1H), 3.63 (d, J=11.6 Hz, 1H), 2.53-2.47 (m, 2H), 1.99-1.84 (m, 10H), 1.78-1.69 (m, 3H), 1.52 (s, 3H), 1.26 (s, 3H), 1.15 (t, J=4.8 Hz, 1H), 1.00-0.97 (m, 1H). HRMS calc. $C_{24}H_{33}N_5O_3Cl$ (M+H)$^+$: 474.2272; found 474.2274.

((3aR,3bR,4aS,5R,5aS)-5-(6-(((1R,2S,4S)-Bicyclo[2.2.1]heptan-2-yl)amino)-2-chloro-9H-purin-9-yl)-2,2-dimethyltetrahydrocyclopropa[3,4]cyclopenta[1,2-d][1,3]dioxol-3b(3aH)-yl)methanol (62)

Compound 62 (91%) was prepared from compound 59 following the same method for compound 60. $^1$H NMR ($CD_3OD$, 400 MHz) δ 8.21 (s, 1H), 5.38 (d, J=6.4 Hz, 1H), 4.95 (s, 1H), 4.69 (d, J=7.2 Hz, 1H), 4.00-3.97 (m, 2H), 3.62 (d, J=12.0 Hz, 1H), 2.35-2.33 (m, 2H), 1.99-1.87 (m, 1H), 1.71-1.67 (m, 1H), 1.61-1.58 (m, 3H), 1.52 (s, 3H), 1.48-1.33 (m, 2H), 1.31-1.22 (m, 5H), 1.14 (t, J=4.8 Hz, 1H), 0.99-0.95 (m, 1H). HRMS calc. $C_{22}H_{29}N_5O_3Cl$ (M+H)$^+$: 446.1959; found 446.1953.

9-((3aR,3bS,4aS,5R,5aS)-3b-(Chloromethyl)-2,2-dimethylhexahydrocyclopropa[3,4]cyclopenta[1,2-d][1,3]dioxol-5-yl)-N-(dicyclobutylmethyl)-9H-purin-6-amine (63)

$SOCl_2$ (0.048 mL, 0.39 mL) was added dropwise to a solution of compound 60 (58 mg, 0.13 mmol) in dry $CH_3CN$ at −5° C. followed by pyridine (32 L, 0.39 mmol) and the solution stirred for 30 min at same condition. Then the reaction mixture was brought to room temperature and stirred for overnight. Water was added into the reaction and the reaction mixture was neutralized with 1M $NaHCO_3$ solution. Aqueous layer was extracted with $CH_2Cl_2$ (3 times), dried over $Na_2SO_4$, filtered and evaporated. The residue was purified by flash silica gel column chromatography (hexane:ethyl acetate=2:1) to afford the compound 63 (37 mg, 62%) as a colorless syrup. $^1$H NMR ($CD_3OD$, 400 MHz) δ 8.39 (s, 1H), 8.37 (s, 1H), 5.41 (d, J=7.2 Hz, 1H), 5.09 (s, 1H), 4.83 (d, J=6.8 Hz, 1H), 4.32 (t, J=6.8 Hz, 1H), 3.93 (d, J=10.4 Hz, 1H), 2.64-2.60 (m, 2H), 2.03-1.85 (m, 10H), 1.80-1.78 (m, 3H), 1.54 (s, 3H), 1.36 (t, J=5.2 Hz, 1H), 1.27 (s, 3H), 1.19-1.15 (m, 1H). HRMS calc. $C_{24}H_{33}N_5O_2Cl$ (M+H)$^+$: 458.2323; found 458.2322.

2-Chloro-9-((3aR,3bS,4aS,5R,5aS)-3b-(chloromethyl)-2,2-dimethylhexahydrocyclopropa[3,4]cyclopenta[1,2-d][1,3]dioxol-5-yl)-N-(dicyclobutylmethyl)-9H-purin-6-amine (64)

Compound 64 (65%) was prepared from compound 61 following the same method for compound 63. $^1$H NMR ($CD_3OD$, 400 MHz) δ 8.15 (s, 1H), 5.38 (d, J=7.2 Hz, 1H), 4.94 (s, 1H), 4.78 (d, J=6.8 Hz, 1H), 4.37 (t, J=8.0 Hz, 1H), 4.15 (d, J=11.6 Hz, 1H), 3.79 (d, J=11.6 Hz, 1H), 2.55-2.49 (m, 2H), 1.99-1.86 (m, 10H), 1.84-1.74 (m, 3H), 1.53 (s, 3H), 1.30-1.27 (m, 4H), 1.14-1.10 (m, 1H). HRMS calc. $C_{24}H_{32}N_5O_2Cl$ (M+H)$^+$: 492.1933; found 492.1935.

N-((1R,2S,4S)-Bicyclo[2.2.1]heptan-2-yl)-2-chloro-9-((3aR,3bS,4aS,5R,5aS)-3b-(chloromethyl)-2,2-dimethylhexahydrocyclopropa[3,4]cyclopenta[1,2-d][1,3]dioxol-5-yl)-9H-purin-6-amine (65)

Compound 65 (63%) was prepared from compound 62 following the same method for compound 63. $^1$H NMR ($CD_3OD$, 400 MHz) δ 8.14 (s, 1H), 5.36 (d, J=7.2 Hz, 1H), 4.94 (s, 1H), 4.77 (d, J=7.2 Hz, 1H), 4.13-4.02 (m, 2H), 3.80 (d, J=11.6 Hz, 1H), 2.35-2.33 (m, 2H), 1.92-1.86 (m, 1H), 1.81-1.77 (m, 1H), 1.64-1.61 (m, 2H), 1.53 (s, 3H), 1.47-1.33 (m, 2H), 1.30-1.23 (m, 7H), 1.14-1.10 (m, 1H). HRMS calc. $C_{22}H_{28}N_5O_2Cl_2$ (M+H)$^+$: 464.1620; found 464.1614.

2-Chloro-N-(dicyclobutylmethyl)-9-((3aR,3bS,4aS,5R,5aS)-3b-(((2-fluorophenyl)thio)methyl)-2,2-dimethylhexahydrocyclopropa[3,4]cyclopenta[1,2-d][1,3]dioxol-5-yl)-9H-purin-6-amine (66)

NaH (5.6 mg, 0.23 mmol) was added portion wise to an ice-cold solution of 2-fluoro-thiophenol (38 mg, 0.07 mmol) in dry DMF (1 mL). After hydrogen evolution completed, compound 64 (29 mg, 0.05 mmol) was added in dry DMF (0.5 mL) and the solution stirred for overnight at room temperature. The reaction mixture was quenched with water and aqueous layer was extracted with ethyl acetate (3 times), dried over $Na_2SO_4$, filtered and evaporated. The residue was purified on flash silica gel column chromatography (hexane:ethyl acetate=1:1) to give the compound 66 (29 mg, 85%) as a syrup. 1H NMR ($CD_3OD$, 400 MHz) δ 8.06 (s, 1H), 7.52-7.48 (m, 1H), 7.21-7.16 (m, 1H), 7.06-7.00 (m, 2H), 5.36 (d, J=6.8 Hz, 1H), 4.81 (s, 1H), 4.79 (d, J=6.8 Hz, 1H), 4.40 (t, J=6.8 Hz, 1H), 3.66 (d, J=12.0 Hz, 1H), 3.29 (d, J=12.0 Hz, 1H), 2.53-2.50 (m, 2H), 2.02-1.84 (m, 10H), 1.78-1.76 (m, 2H), 1.58-1.52 (m, 1H), 1.52 (s, 3H), 1.26 (m, 3H), 1.11 (t, J=5.2 Hz, 1H), 0.97-0.93 (m, 1H). HRMS calc. $C_{30}H_{36}N_5O_2ClSF$ (M+H)$^+$: 584.2262; found 584.2271.

(2R,3R,4R,5R)-2-((Benzoyloxy)methyl)-5-(6-((dicyclobutylmethyl)amino)-9H-purin-9-yl)tetrahydrofuran-3,4-diyl dibenzoate (69)

Compound 69 (91%) was prepared from compound 67 following the same method for compound 57. $^1$H NMR ($CD_3OD$, 400 MHz) δ 8.26 (s, 1H), 8.08 (s, 1H), 8.06-7.93 (m, 6H), 7.64-7.57 (m, 3H), 7.48-7.37 (m, 6H), 6.54-6.49 (m, 2H), 6.36 (t, J=5.6 Hz, 1H), 4.92-4.91 (m, 2H), 4.73 (dd, $J_1$=3.2 Hz, $J_2$=8.0 Hz, 1H), 4.37 (br s, 1H), 2.55-2.49 (m, 2H), 1.97-1.85 (m, 10H), 1.83-1.76 (m, 2H). HRMS calc. $C_{40}H_{40}N_5O_7$ (M+H)$^+$: 702.2928; found 702.2919.

(2R,3R,4R,5R)-2-((Benzoyloxy)methyl)-5-(2-chloro-6-((dicyclobutylmethyl)amino)-9H-purin-9-yl)tetrahydrofuran-3,4-diyl dibenzoate (70)

Compound 70 (89%) was prepared from compound 68 following the same method for compound 57. $^1$H NMR (CD$_3$OD, 400 MHz) δ 8.21 (s, 1H), 8.04-7.94 (m, 6H), 7.63-7.57 (m, 3H), 7.46-7.37 (m, 6H), 6.50 (d, J=4.0 Hz, 1H), 6.35-6.28 (m, 2H), 4.75-4.71 (m, 1H), 4.36 (t, J=8.0 Hz, 1H), 2.51-2.46 (m, 2H), 1.98-1.87 (m, 10H), 1.82-1.75 (m, 2H). HRMS calc. $C_{40}H_{39}N_5O_7Cl$ (M+H)$^+$: 736.2538; found 736.2526.

((3aR,4R,6R,6aR)-6-(6-((Dicyclobutylmethyl)amino)-9H-purin-9-yl)-2,2-dimethyltetrahydrofuro[3,4-d][1,3]dioxol-4-yl)methanol (71)

2,2-Dimethoxypropane (0.31 mL, 2.57 mmol) and p-toluenesulfonic acid (97 mg, 0.51 mmol) were added to a solution of compound 9 (200 mg, 0.51 mmol) in acetone (10 mL) and stirred for 5 h at room temperature. Reaction mixture was neutralized with NaHCO$_3$, filtered and evaporated. The residue was purified on flash silica gel column chromatography (hexane:ethyl acetate=1:2) to give the compound 71 (211 mg, 96%) as a colorless syrup.

9-((3aR,4R,6S,6aS)-6-(Chloromethyl)-2,2-dimethyltetrahydrofuro[3,4-d][1,3]dioxol-4-yl)-N-(dicyclobutylmethyl)-9H-purin-6-amine (72)

Compound 72 (67%) was prepared from compound 71 following the same method as for compound 63. $^1$H NMR (CD$_3$OD, 400 MHz) δ 8.25 (s, 2H), 6.24 (d, J=2.4 Hz, 1H), 5.50 (d, J$_1$=2.4 Hz, J$_2$=4.4 Hz, 1H), 5.16 (d, J, =2.4 Hz, J$_2$=6.0 Hz, 1H), 4.45-4.37 (m, 2H), 3.84 (d, J$_1$=4.4 Hz, J$_2$=7.2 Hz, 1H), 3.70 (d, J$_1$=4.4 Hz, J$_2$=7.2 Hz, 1H), 2.54-2.50 (m, 2H), 2.02-1.83 (m, 10H), 1.76-1.75 (m, 2H), 1.61 (s, 3H), 1.40 (s, 3H). HRMS calc. $C_{22}H_3N_5O_3Cl$ (M+H)$^+$: 448.2115; found 448.2113.

N-(Dicyclobutylmethyl)-9-((3aR,4R,6S,6aS)-6-((ethylthio)methyl)-2,2-dimethyltetrahydrofuro[3,4-d][1,3]dioxol-4-yl)-9H-purin-6-amine (73)

Sodium thioethoxide (27.8 mg, 0.33 mmol) was added to a solution of compound 72 (37 mg, 0.08 mmol) in dry DMF (1 mL) at 0° C. and the solution stirred at room temperature for 1 h. The reaction mixture was quenched with water and the aqueous layer was extracted with ethyl acetate (3 times), dried over Na$_2$SO$_4$, filtered and evaporated. The residue was purified on flash silica gel column chromatography (hexane:ethyl acetate=2:1) to give the compound 73 (34 mg, 87%) as a syrup. $^1$H NMR (CD$_3$OD, 400 MHz) δ 8.26 (s, 1H), 8.25 (s, 1H), 6.19 (d, J=2.4 Hz, 1H), 5.56 (d, J$_1$=1.6 Hz, J$_2$=4.8 Hz, 1H), 5.08 (m, 1H), 4.39-4.26 (m, 2H), 2.82-2.80 (m, 2H), 2.55-2.46 (m, 4H), 2.01-1.83 (m, 10H), 1.77-1.75 (m, 2H), 1.60 (s, 3H), 1.40 (s, 3H), 1.14 (t, J=7.2 Hz, 3H). HRMS calc. $C_{24}H_{36}N_5O_3S$ (M+H)$^+$: 474.2539; found 474.2541.

(1R,2R,3S,4R,5S)-4-(4-(((1R,2S,4S)-Bicyclo[2.2.1]heptan-2-yl)amino)-6-chloro-1H-imidazo[4,5-c]pyridin-1-yl)-1-(hydroxymethyl)bicyclo[3.1.0]hexane-2,3-diol (30)

A solution of compound 79 (48 mg, 0.07 mmol) in methanol (3 mL) and 10% TFA in water (3 mL) was heated at 70° C. for overnight. Solvent was evaporated under vacuum and the residue was purified on flash silica gel silica chromatography (hexane:ethyl acetate=1:2) to give the compound 30 (21 mg, 77%) as a syrup. $^1$H NMR (CD$_3$OD, 400 MHz) δ 8.18 (s, 1H), 6.87 (s, 1H), 5.05 (d, J=11.6 Hz, 1H), 4.63 (s, 1H), 4.53 (d, J=6.4 Hz, 1H), 4.29 (d, J=11.6 Hz, 1H), 4.00 (m, 1H), 3.88 (d, J=6.4 Hz, 1H), 2.34-2.33 (m, 2H), 2.02-1.98 (s, 1H), 1.92-1.87 (m, 1H), 1.79 (d, J=4.8 Hz, 1H), 1.61-1.54 (m, 3H), 1.42-1.35 (m, 2H), 1.26-1.23 (m, 2H), 1.03-0.98 (m, 1H). HRMS calculated for $C_{20}H_{26}N_4O_3Cl$ (M+H)+: 405.1693; found 405.1692.

Ethyl (1S,2R,3S,4R,5S)-4-(2-Chloro-6-((dicyclobutylmethyl)amino)-9H-purin-9-yl)-2,3-dihydroxybicyclo[3.1.0]hexane-1-carboxylate (35)

Compound 35 (89%) was prepared from compound 82 following the same method as for compound 24. $^1$H NMR (CD$_3$OD, 400 MHz) δ 7.97 (s, 1H), 5.24 (d, J=6.8 Hz, 1H), 4.77 (s, 1H), 4.36 (t, J=8.0 Hz, 1H), 4.28-4.23 (m, 2H), 4.11 (d, J=6.4 Hz, 1H), 2.52-2.48 (m, 2H), 2.19-2.16 (m, 1H), 1.99-1.82 (m, 11H), 1.77-1.74 (m, 2H), 1.63-1.64 (m, 1H), 1.32 (t, J=7.2 Hz, 3H). HRMS calculated for $C_{23}H_{31}N_5O_4Cl$ (M+H)$^+$: 476.2065; found 476.2068.

(1S,2R,3S,4R,5S)-4-(6-(((1R,2S,4S)-bicyclo[2.2.1]heptan-2-yl)amino)-2-chloro-9H-purin-9-yl)-N-cyclopropyl-2,3-dihydroxybicyclo[3.1.0]hexane-1-carboxamide (36)

Compound 36 (92%) was prepared from compound 75 following the same method as for compound 24. $^1$H NMR (CD$_3$OD, 400 MHz) δ 8.08 (s, 1H), 5.07 (d, J=6.8 Hz, 1H), 4.79 (s, 1H), 4.01-3.99 (m, 2H), 2.77-2.72 (m, 1H), 2.34-2.33 (m, 2H), 2.08-2.04 (m, 1H), 1.92-1.83 (m, 1H), 1.81 (t, J=4.8 Hz, 1H), 1.60-1.51 (m, 3H), 1.47-1.43 (m, 1H), 1.39-1.34 (m, 2H), 1.28-1.21 (m, 2H), 0.78-0.77 (m, 2H), 0.67-0.58 (m, 2H). HRMS calculated for $C_{22}H_{28}N_6O_3Cl$ (M+H)$^+$: 459.1911; found 459.1915.

(1S,2R,3S,4R,5S)-4-(6-(((1R,2S,4S)-bicyclo[2.2.1]heptan-2-yl)amino)-2-chloro-9H-purin-9-yl)-2,3-dihydroxy-N-(2-hydroxyethyl)bicyclo[3.1.0]hexane-1-carboxamide (37)

Compound 37 (89%) was prepared from compound 76 following the same method as for compound 24. $^1$H NMR (CD$_3$OD, 400 MHz) δ 8.05 (s, 1H), 7.76 (t, J=5.2 Hz, 1H), 5.01 (d, J=6.4 Hz, 11H), 4.81 (s, 11H), 4.01-3.99 (m, 2H), 3.63 (t, J=6.0 Hz, 2H), 3.46 (d, J=5.6 Hz, 2H), 2.35-2.33 (m, 2H), 2.12-2.09 (m, 1H), 1.92-1.85 (m, 2H), 1.64-1.52 (m, 3H), 1.48-1.43 (m, 1H), 1.39-1.34 (m, 2H), 1.30-1.21 (m, 2H). HRMS calculated for $C_{21}H_{28}N_6O_4Cl$ (M+H)$^+$: 463.1861; found 463.1860.

Methyl 1-((1S,2R,3S,4R,5R)-3,4-dihydroxy-5-(hydroxymethyl)bicyclo[3.1.0]hexan-2-yl)-1H-1,2,4-triazole-3-carboxylate (39)

Compound 39 (82%) was prepared from compound 80 following the same method as for compound 30. $^1$H NMR (CD$_3$OD, 400 MHz) δ 8.09 (s, 1H), 5.57 (s, 1H), 4.83 (d, J=6.4 Hz, 1H), 4.13 (d, J=6.4 Hz, 1H), 4.02 (s, 3H), 3.94 (d, J=11.6 Hz, 1H), 3.55 (d, J=11.6 Hz, 1H), 1.49-1.43 (m, 2H), 0.79-0.76 (m, 1H). HRMS calculated for $C_{11}H_{15}N_3O_5Na$ (M+Na)$^+$: 292.0909; found 292.0910.

1-((1S,2R,3S,4R,5R)-3,4-Dihydroxy-5-(hydroxymethyl)bicyclo[3.1.0]hexan-2-yl)-1H-1,2,4-triazole-3-carboxamide (40)

A solution of compound 39 (15 mg, 0.055 mmol) in saturated methanolic ammonia (3 mL) was stirred overnight at room temperature. Solvent was evaporated and the residue was purified by flash silica gel column chromatography (CH$_2$Cl$_2$:MeOH:Et$_3$N=20:1:0.1) to give the compound 40 (10 mg, 74%) as colorless powder. $^1$H NMR (CD$_3$OD, 400 MHz) δ 7.98 (s, 1H), 5.74 (s, 1H), 4.84 (d, J=6.8 Hz, 1H), 4.09 (d, J=6.4 Hz, 1H), 3.95 (d, J=11.6 Hz, 1H), 1.47-1.37 (m, 2H), 0.77-0.74 (m, 1H). HRMS calculated for C$_{10}$H$_{14}$N$_4$O$_4$Na (M+Na)$^+$: 277.0913; found 277.0908.

(3aR,3bS,4aS,5R,5aS)-5-(6-(((1R,2S,4S)-bicyclo[2.2.1]heptan-2-yl)amino)-2-chloro-9H-purin-9-yl)-2,2-dimethyltetrahydrocyclopropa[3,4]cyclopenta[1,2-d][1,3]dioxole-3b(3aH)-carboxylic Acid (74)

TEMPO (9.1 mg, 0.005 mmol) and BAIB (206 mg, 0.64 mmol) were added to a solution of compound 62 (130 mg, 0.29 mmol) in CH$_3$CN (2 mL) and water (2 mL) and stirred for 3 days at room temperature. The aqueous layer was extracted with ethyl acetate (3 times), dried (Na$_2$SO$_4$), filtered and evaporated under vacuum. The crude mixture was purified on flash silica gel column chromatography (CH$_2$Cl$_2$:MeOH=30:1) to give the compound 74 (70 mg, 53%) as a syrup. $^1$H NMR (CD$_3$OD, 400 MHz) δ 8.02 (s, 1H), 5.85 (d, J=6.8 Hz, 1H), 4.98 (s, 1H), 4.81 (d, J=7.2 Hz, 1H), 4.02 (br s, 1H), 2.35-2.33 (m, 2H), 2.25-2.21 (m, 1H), 1.92-1.87 (m, 1H), 1.70-1.67 (m, 1H), 1.61-1.58 (m, 2H), 1.54-1.51 (m, 5H), 1.47-1.35 (m, 2H), 1.28-1.21 (m, 5H). HRMS calculated for C$_{22}$H$_{27}$N$_5$O$_3$Cl (M+H)$^+$: 444.1802; found 444.1809.

(3aR,3bS,4aS,5R,5aS)-5-(6-(((1R,2S,4S)-bicyclo[2.2.1]heptan-2-yl)amino)-2-chloro-9H-purin-9-yl)-N-cyclopropyl-2,2-dimethyltetrahydrocyclopropa[3,4]cyclopenta[1,2-d][1,3]dioxole-3b(3aH)-carboxamide (75)

Cyclopropylamine (6.3 μL, 0.09 mmol), HATU (38 mg, 0.1 mmol) and DIPEA (0.17 mL, 0.1 mmol) were added to a solution of compound 74 (35 mg, 0.07 mmol) in dry DMF (1 mL) and stirred for overnight at room temperature. Solvent was evaporated under vacuum and the residue was purified on flash silica gel column chromatography (hexane:ethyl acetate=1:1) to give the compound 75 (28 mg, 72%) as syrup. $^1$H NMR (CD$_3$OD, 400 MHz) δ 8.05 (s, 1H), 5.76 (d, J=7.2 Hz, 1H), 4.94 (s, 1H), 4.84 (d, J=7.2 Hz, 1H), 4.01 (br s, 1H), 2.72-2.68 (m, 1H), 2.34-2.32 (m, 2H), 2.16-2.12 (m, 1H), 1.91-1.86 (m, 1H), 1.60-1.53 (m, 6H), 1.46-1.36 (m, 2H), 1.34-1.23 (m, 6H), 0.76-0.73 (m, 2H), 0.67-0.61 (m, 2H). HRMS calculated for C$_{25}$H$_{32}$N$_6$O$_3$Cl (M+H)$^+$: 499.2224; found 499.2218.

(3aR,3bS,4aS,5R,5aS)-5-(6-(((1R,2S,4S)-bicyclo[2.2.1]heptan-2-yl)amino)-2-chloro-9H-purin-9-yl)-N-(2-hydroxyethyl)-2,2-dimethyltetrahydrocyclopropa[3,4]cyclopenta[1,2-d][1,3]dioxole-3b(3aH)-carboxamide (76)

Compound 76 (70%) was prepared from compound 74 following the same method as for compound 75. $^1$H NMR (CD$_3$OD, 400 MHz) δ 8.06 (s, 1H), 5.78 (d, J=7.2 Hz, 1H), 4.97 (s, 1H), 4.84 (d, J=7.2 Hz, 1H), 4.01 (br s, 1H), 3.67 (t, J=6.0 Hz, 2H), 3.53-3.47 (m, 2H), 2.35-2.32 (m, 2H), 2.18-2.14 (m, 1H), 1.92-1.87 (m, 1H), 1.61-1.54 (m, 6H), 1.48-1.47 (m, 1H), 1.43-1.41 (m, 2H), 1.38-1.32 (m, 1H), 1.30-1.24 (m, 5H). HRMS calculated for C$_{24}$H$_{31}$N$_6$O$_4$Cl (M+H)$^+$: 503.2095; found 503.2048.

1-((3aR,3bR,4aS,5R,5aS)-3b-(((tert-butyldiphenylsilyl)oxy)methyl)-2,2-dimethylhexahydrocyclopropa[3,4]cyclopenta[1,2-d][1,3]dioxol-5-yl)-4,6-dichloro-1H-imidazo[4,5-c]pyridine (78)

DIAD (0.14 mL, 0.70 mmol) was added to a solution of 3-deaza-2,6-dichloropurine (134 mg, 0.70 mmol) and triphenylphosphine (186 mg, 0.70 mmol) in THF (3 mL) at 0° C. and the mixture was stirred for 20 minutes at room temperature. A solution of compound 77 (156 mg, 0.35 mmol) in THF (2 mL) was added into the reaction mixture and stirred for overnight at room temperature. Solvent was evaporated and the residue was purified on flash silica gel column chromatography (hexane:ethyl acetate=5:1) to give the compound 78 (109 mg, 50%) as colorless foamy solid. 1H NMR (CD$_3$OD, 400 MHz) δ 8.54 (s, 1H), 7.98 (s, 1H), 7.71-7.66 (m, 4H), 7.46-7.36 (m, 6H), 5.35 (d, J=6.4 Hz, 1H), 5.01 (s, 1H), 4.71 (d, J=6.4 Hz, 1H), 4.23 (d, J=11.2 Hz, 1H), 3.59 (d, J=11.2 Hz, 1H), 1.86-1.83 (m, 1H), 1.52 (s, 3H), 1.29 (s, 3H), 1.21 (t, J=5.2 Hz, 1H), 1.13 (s, 9H), 0.97-0.94 (m, 1H). HRMS calculated for C$_{32}$H$_{36}$N$_3$O$_3$Cl$_2$Si (M+H)$^+$: 608.1903; found 608.1896.

N-((1R,2S,4S)-Bicyclo[2.2.1]heptan-2-yl)-1-((3aR,3bR,4aS,5R,5aS)-3b-(((tert-butyldiphenylsilyl)oxy)methyl)-2,2-dimethylhexahydrocyclopropa[3,4]cyclopenta[1,2-d][1,3]dioxol-5-yl)-6-chloro-1H-imidazo[4,5-c]pyridin-4-amine (79)

(1R, 2S, 4S)-Bicyclo[2.2.1]nonane (105 mg, 0.9 mmol) and DIPEA (0.31 mL, 1.8 mmol) were added to a solution of compound 78 (109 mg, 0.18 mmol) in 2-propanol and heated at 130° C. for 6 hours under microwave condition. Solvent was evaporated under vacuum and the residue was purified on flash silica gel column chromatography (hexane:ethyl acetate=4:1) to give the compound 79 (89 mg, 73%) as a colorless syrup. $^1$H NMR (CD$_3$OD, 400 MHz) δ 8.54 (s, 1H), 7.73-7.68 (m, 4H), 7.47-7.37 (m, 6H), 6.79 (s, 1H), 5.35 (d, J=7.2 Hz, 1H), 4.83 (s, 1H), 4.58 (d, J=7.2 Hz, 1H), 4.25 (d, J=7.2 Hz, 1H), 4.01-3.98 (m, 1H), 3.49 (d, J=7.2 Hz, 1H), 2.37-2.32 (m, 2H), 1.92-1.87 (m, 1H), 1.83-1.80 (m, 1H), 1.61-1.57 (m, 3H), 1.52 (s, 3H), 1.43-1.35 (m, 2H), 1.27-1.23 (m, 5H), 1.18 (t, J=4.8 Hz, 1H), 1.19 (s, 9H), 0.92-0.89 (m, 1H). HRMS calculated for C$_{39}$H$_{48}$N$_4$O$_3$C$_{12}$Si (M+H)$^+$: 683.3184; found 683.3179.

Methyl 1-((3aR,3bR,4aS,5R,5aS)-3b-(((tert-butyldiphenylsilyl)oxy)methyl)-2,2-dimethylhexahydrocyclopropa[3,4]cyclopenta[1,2-d][1,3]dioxol-5-yl)-1H-1,2,4-triazole-3-carboxylate (80)

Compound 80 (68%) was prepared from compound 77 following the same method as for compound 78. $^1$H NMR (CD$_3$OD, 400 MHz) δ 8.02 (s, 1H), 7.64-7.61 (m, 4H), 7.44-7.32 (m, 6H), 5.72 (s, 1H), 5.27 (d, J=6.8 Hz, 1H), 4.88 (s, 1H), 4.01-3.99 (m, 4H), 3.63 (d, J=10.8 Hz, 1H), 1.52 (s, 3H), 1.46-1.43 (m, 1H), 1.25 (s, 3H), 1.10-1.04 (m, 10H), 0.83-0.79 (in, 1H). HRMS calculated for C$_{30}$H$_{38}$N$_3$O$_5$Si (M+H)$^+$: 548.2581; found 548.2574.

Ethyl (3aR,3bS,4aS,5R,5aS)-5-(2-Chloro-6-((dicyclobutylmethyl)amino)-9H-purin-9-yl)-2,2-dimethyltetrahydrocyclopropa[3,4]cyclopenta[1,2-d][1,3]dioxole-3b(3aH)-carboxylate (82)

Compound 82 (85%) was prepared from compound 81 following the same method as for compound 57. $^1$H NMR (CD$_3$OD, 400 MHz) δ 8.04 (s, 1H), 5.86 (d, J=7.2 Hz, 1H), 4.97 (s, 1H), 4.82 (d, J=7.2 Hz, 1H), 4.36 (t, J=8.0 Hz, 1H), 4.29-4.20 (m, 2H), 2.52-2.48 (m, 2H), 2.28-2.24 (m, 1H), 1.90-1.87 (m, 10H), 1.77-1.71 (m, 2H), 1.68-1.64 (m, 1H), 1.55-1.52 (m, 4H), 1.33 (t, J=7.2 Hz, 3H), 1.28 (s, 3H). HRMS calculated for C$_{26}$H$_{35}$N$_5$O$_4$Cl (M+H)$^+$: 516.2299; found 516.2246.

Example 2

This example demonstrates binding affinities of adenosine receptor (AR) ligands to the compounds indicated, including reference compounds 1-7 and 15-18.

Binding was determined in membranes of CHO or HEK293 (A$_{2A}$ only) cells stably expressing one of three hAR subtypes, unless noted (n=3-5). The binding affinity for hA$_1$, A$_{2A}$ and A$_3$ARs was expressed as K$_i$ values using agonists [$^3$H]N$^6$—R-phenylisopropyladenosine 51, [$^3$H]2-[p-(2-carboxyethyl)phenyl-ethylamino]-5'-N-ethylcarboxamidoadenosine 52, or [$^{125}$I]N$^6$-(4-amino-3-iodobenzyl)adenosine-5'-N-methyluronamide 53, respectively. A percent in italics refers to inhibition of binding at 10 μM. Nonspecific binding was determined using adenosine 5'-N-ethyluronamide 54 (10 μM). Values are expressed as the mean±SEM (n=3, unless noted). K$_i$ values were calculated as reported.[42] Off-target interactions determined by the PDSP. Receptor abbreviations as follows: serotonin receptors (5HTRs); dopamine receptors (DRs); rat brain benzodiazepine receptors (BZP); GABA receptors, dopamine transporter (DAT); norepinephrine transporter (NET); TSPO (translocator protein); adrenergic receptors (α- and β-); muscarinic receptors (MRs); delta (DOR), kappa (KOR), and mu (MOR) opioid receptors; sigma receptors (σ); and histamine receptors (HRs). Gp, guinea pig.

TABLE 1

Adenosine Receptor Binding for Ribose Analogs

| Cmpd | R$^1$ | R$^2$ | R$^3$ | A$_1$AR % inhibition or K$_i$ (nM)$^a$ | A$_{2A}$AR % inhibition$^a$ | A$_3$AR % inhibition or K$_i$ (nM)$^a$ | Off-target, receptor (h, unless noted) (K$_i$, μM)$^a$ |
|---|---|---|---|---|---|---|---|
| 1a$^{c,d}$ | cyclopentyl | H | OH | 2.3 (h), 0.22 ± 0.01 (m) | 794 (h), 808 ± 89 (m) | 72 ± 12 (h), 534 ± 14 (m) | ND |
| 2$^{c,d}$ | cyclopentyl | Cl | OH | 0.83 (h), 0.21 ± 0.10 (m) | 2270 (h), 988 (m) | 38 ± 6 (h), 17 ± 5 (m) | ND |
| 5$^f$ | 2-hydroxycyclopentyl | H | 2-F—Ph | 12 (h) | >10,000 (h) | >1000 (h) | ND |
| 8$^b$ | dicyclopropylmethyl | H | OH | 0.85 ± 0.27 (h), 0.8 (r) | 1470 ± 380 (h), 1370 (r) | 41.3 ± 5.3 (h) | none |
| 9 | cyclobutyl/cyclopropyl methyl | H | OH | 2.14 ± 0.52 (h), 0.37 ± 0.02 (m) | 3550 ± 440 (h) | 10,600 ± 1400 (h), 897 ± 45 (m) | DAT 1.78, NET 4.82 |

TABLE 1-continued

Adenosine Receptor Binding for Ribose Analogs

| Cmpd | R¹ | R² | R³ | $A_1AR$ % inhibition or $K_i$ (nM)$^a$ | $A_{2A}AR$ % inhibition$^a$ | $A_3AR$ % inhibition or $K_i$ (nM)$^a$ | Off-target, receptor (h, unless noted) ($K_i$, μM)$^a$ |
|---|---|---|---|---|---|---|---|
| 10 | dicyclobutylmethyl | H | Cl | 4.90 ± 0.87 (h), 0.71 ± 0.12 (m) | 5200$^i$ (h) | 16,600 ± 2000 (h), 2110 ± 50 (m) | TSPO 3.98, $\sigma_1$ 0.69, $\sigma_2$ 0.662 |
| 11 | dicyclobutylmethyl | H | —SEt | 63.4 ± 12.1 (h), 3.58 ± 0.01 (m) | 30 ± 5% (h) | 6220 ± 1480 (h), 718 ± 150 (m) | TSPO (90% inhib.$^j$) $\sigma_1$ 0.626, $\sigma_2$ 0.642 |
| 12 | dicyclobutylmethyl | Cl | OH | 17.8 ± 8.7 (h), 0.65 ± 0.06 (m) | 2550 ± 540 (h) | 13,200 ± 2500 (h), 653 ± 85 (m) | 5HT$_{2C}$ 1.45 |
| 3$^{c,d}$ | norbornyl | H | Cl | 0.38 ± 0.19 (h), 0.34 (r), 0.14 ± 0.02 (m) | >10,000 (h), 477 (r) | 915 ± 299 (h), 282 (r), 424 ± 41 (m) | ND |
| 4$^c$ | norbornyl | H | Cl | 0.51 (h), 0.20 ± 0.01 (m) | 1340 (h), 3990 ± 360 (m) | 1290 (h), 2410 ± 330 (m) | ND |
| 13$^c$ | norbornyl | H |  | 0.76 ± 0.42 (h) | 2050 ± 570 (h) | 355 ± 117 (h), 1560 ± 140 (m) | $\sigma_1$ 0.484, $\sigma_2$ 0.432, 5HT$_7$ 1.24 |

TABLE 2

Adenosine Receptor Binding for Ribose Analogs

| Cmpd | R[1] | R[2] | R[4] | $A_1AR$ % inhibition or $K_i$ (nM)[a] | $A_{2A}AR$ % inhibition[a] | $A_3AR$ % inhibition or $K_i$ (nM)[a] | Off-target, receptor (h, unless noted) ($K_i$, μM)[a] |
|---|---|---|---|---|---|---|---|
| 14 | H | H | OH | 24 ± 4% (h) | 11 ± 4% (h) | 32 ± 9% (h) | BZP (r) 7.34, σ₁ 1.48, σ₂ 0.796 |
| 15[d] | H | H | NHMe | 36.7 ± 9.4 (h), 84 (r) | 466 ± 95 (h), 67 (r) | 24.4 ± 7.9 (h), 63 (r) | none |
| 16[c,d,b] | H | H | NHEt | 6.8 ± 2.4 (h),g 3.00 ± 0.10 (h), 0.45 ± 0.13 (m), 63 (r) | 2.2 ± 0.6 (h),g 35.0 ± 14.0 (h), 12 (r) | 35 ± 12 (h), 14.1 ± 6.8(m), 113 (r) | none |
| 17[c,d] | H | H | NH-c-Pr | 1.90 ± 0.60 (h), 6.4 (r) | 50 ± 10 (h), 13.4 (r) | 180 ± 50 (h), 1600 (r) | H₁ 7.88, σ₁ 4.12 (gp), σ₂ 4.35 |
| 18[d,h] | H | H | NH(CH₂)₂OH | 12.8 ± 3.1 (h) | 505 ± 30 (h) | 9450 ± 1760 (h) | ND |

TABLE 3

Adenosine Receptor Binding for "Truncated" Methanocarba Analogs

| Cmpd | R[1] | R[2] | $A_1AR$ % inhibition or $K_i$ (nM)[a] | $A_{2A}AR$ % inhibition[a] | $A_3AR$ % inhibition or $K_i$ (nM)[a] | Off-target, receptor (h, unless noted) ($K_i$, μM)[a] |
|---|---|---|---|---|---|---|
| 7[c] | dicyclopropylmethyl | Cl | 47.9 ± 10.5 (h), 5.20 ± 0.05 (m) | 3950 ± 410 (h), 34 ± 9% (m) | 470 ± 15 (h), 1060 ± 250 (m) | 5HT$_{2B}$ 0.641, 5HT$_{2C}$ 1.85 |
| 19 | dicyclobutylmethyl | Cl | 961 ± 639 (h) | 46 ± 6% (h) | 822 ± 449 (h), 385 ± 52 (m) | 5HT$_{2B}$ 2.90, 5HT$_{2C}$ 8.32, α$_{2A}$ 6.96, TSPO 2.38 |
| 29[c] | dicyclopentylmethyl | Cl | 34 ± 3% (h) | 13 ± 3% (h) | 48 ± 2% (h) | 5HT$_{2C}$ 2.92, σ₁ 5.09, σ₂ 2.01 |

TABLE 4

Adenosine Receptor Binding for Hydroxymethyl and Chloromethyl Methanocarba Analogs

| Cmpd | R[1] | R[2] | R[3] | $A_1AR$ % inhibition or $K_i$ (nM)[a] | $A_{2A}AR$ % inhibition[a] | $A_3AR$ % inhibition or $K_i$ (nM)[a] | Off-target, receptor (h, unless noted) ($K_i$, μM)[a] |
|---|---|---|---|---|---|---|---|
| 21[b] | H | Cl | OH | 105 ± 63 (h), 273 (r)[b] | 3420 ± 270 (h), 1910 (r)[b] | 353 ± 54 (h)[d] | none |

TABLE 4-continued

Adenosine Receptor Binding for Hydroxymethyl and Chloromethyl Methanocarba Analogs

| Cmpd | R¹ | R² | R³ | $A_1AR$ % inhibition or $K_i$ (nM)[a] | $A_{2A}AR$ % inhibition[a] | $A_3AR$ % inhibition or $K_i$ (nM)[a] | Off-target, receptor (h, unless noted) ($K_i$, µM)[a] |
|---|---|---|---|---|---|---|---|
| 22 | H | Cl | Cl | 7.61 ± 0.73 (h) | 1750 ± 290 (h) | 253 ± 148 (h) | σ₁ 1.97, σ₂ 2.55 |
| 23[b] | cyclopropyl,cyclopropyl | Cl | | 39 ± 17 (h), 0.71 ± 0.06 (m) | 2200 (h), 41 ± 9% | 1600 ± 210 (h), 1030 ± 40 (m) | 5HT$_{2B}$ 0.641, 5HT$_{2C}$ 1.85, DAT 4.75 |
| 24 | cyclobutyl,cyclobutyl | H | | 22.7 ± 3.0 (h), 0.53 ± 0.19 (m) | 34 ± 1% (h) | 51 ± 6% (h), 918 ± 21 (m) | BZP (r) 4.08, 5HT$_{2B}$ 0.214, 5HT$_{2C}$ 1.32, σ₁ 1.79, σ₂ 0.753 |
| 25 | cyclobutyl,cyclobutyl | Cl | | 8.96 ± 1.02 (h), 2.47 ± 0.26 (m) | 55 ± 5% (h), 26 ± 3% (m) | 25 ± 2% (h), 612 ± 58 (m) | 5HT$_{2B}$ 0.153, 5HT$_{2C}$ 0.238, M₅ 3.00, DAT 4.75 TSPO 2.93 |
| 26 | cyclobutyl,cyclobutyl | H | Cl | 32.7 ± 12.4 (h), 1.05 ± 0.19 (m) | 38 ± 3% (h) | 49 ± 4% (h), 934 ± 18 (m) | 5HT$_{2B}$ 2.01, α$_{2A}$ 6.80, σ₁ 1.50, σ₂ 1.17, TSPO, 2.02 |
| 27 | cyclobutyl,cyclobutyl | Cl | Cl | 120 ± 23 (h), 11.2 ± 0.8 (m) | 17 ± 24% (h), 20 ± 3% (m) | 3820 ± 1820 (h), 1560 ± 60 (m) | 5HT$_{2B}$ 1.52, 5HT$_{2C}$ 1.75, H₂ 2.60, σ₂ 0.349, TSPO, 2.89 |
| 28 | cyclobutyl,cyclobutyl | Cl | S—(2-F—Ph) | 45 ± 4% (h), 2490 ± 280 (m) | 22 ± 5% (h), 20 ± 9% (m) | 9750 ± 4030 (h), 7440 ± 660 (m) | 5HT$_{2B}$ 0.334, 5HT$_{2C}$ 1.46, σ₂ 0.583 |

TABLE 4-continued

Adenosine Receptor Binding for Hydroxymethyl and Chloromethyl Methanocarba Analogs

| Cmpd | R¹ | R² | R³ | $A_1AR$ % inhibition or $K_i$ (nM)[a] | $A_{2A}AR$ % inhibition[a] | $A_3AR$ % inhibition or $K_i$ (nM)[a] | Off-target, receptor (h, unless noted) ($K_i$, μM)[a] |
|---|---|---|---|---|---|---|---|
| 29 | norbornyl | Cl | OH | 23.6 ± 5.2 (h), 1.05 ± 0.03 (m) | 4260[i] (h), 15 ± 2% (m) | 288 ± 54 (h), 574 ± 23 (m) | $5HT_{2B}$ 0.472, NET 5.74 |
| 30 (Y = N) | norbornyl | Cl | OH | 240 ± 19 (h) | 29 ± 13% (h) | 145 ± 74 (h) | none |
| 31 | norbornyl | Cl | Cl | 44.8 ± 1.3 (h), 1.86 ± 0.10 (m) | 54 ± 8% (h), 15 ± 1% (m) | 456 ± 201 (h), 503 ± 13 (m) | none |

TABLE 5

Adenosine Receptor Binding for Ester and Amido Methanocarba Analogs

| Cmpd | R¹ | R² | R⁴ | $A_1AR$ % inhibition or $K_i$ (nM)[a] | $A_{2A}AR$ % inhibition[a] | $A_3AR$ % inhibition or $K_i$ (nM)[a] | Off-target, receptor (h, unless noted) ($K_i$, μm)[a] |
|---|---|---|---|---|---|---|---|
| 32[b] | dicyclopropylmethyl | Cl | OEt | 360 ± 74 (h) | 1570 ± 180 (h) | 236 ± 41 (h) | $5HT_{2B}$ 0.015, $5HT_{2C}$ 0.054, TSPO 2.50 |

TABLE 5-continued

Adenosine Receptor Binding for Ester and Amido Methanocarba Analogs

[Chemical structure: purine nucleoside analog with HN-R¹ at 6-position, R² at 2-position of purine, attached to a bicyclic methanocarba scaffold bearing R⁴C(O)-, R³, and R⁴ substituents]

| Cmpd | R¹ | R² | R⁴ | $A_1AR$ % inhibition or $K_i$ (nM)[a] | $A_{2A}AR$ % inhibition[a] | $A_3AR$ % inhibition or $K_i$ (nM)[a] | Off-target, receptor (h, unless noted) ($K_i$, μm)[a] |
|---|---|---|---|---|---|---|---|
| 33[b] (2',3'-C(Me₃)₂ (see below) | dicyclopropylmethyl | Cl | OEt | 49 ± 9% (h) | 15 ± 2% (h) | 41 ± 6% (h) | $5HT_{5A}$ 8.69, $H_2$ 6.38 |
| 34[b] | dicyclopropylmethyl | Cl | NHMe | 110 ± 14 (h) | 4320 ± 1870 (h) | 34 ± 11 (h) | $5HT_{2B}$ 0.023, $5HT_{2C}$ 0.749 |
| 35 | dicyclobutylmethyl | Cl | OEt | 73.8 ± 14.2 (h) | 57 ± 12% (h) | 1160 ± 300 (h) | $5HT_{2B}$ 0.097, $5HT_{2C}$ 0.089, $M_3$ 5.90, $σ_2$ 2.02 |
| 6e | cyclopentylmethyl | Cl | NHMe | 18.3 ± 6.3 (h), 0.68 ± 0.02 (m) | 3250 ± 300 (h) | 3.7 ± 0.9 (h), 5.8 ± 1.6 (r), 3.46 ± 0.13 (m) | $5HT_{2B}$ 0.012, $σ_1$ 1.55 |
| 36 | norbornyl | Cl | NH-c-Pr | 1.22 ± 0.05 (h), 0.45 ± 0.03 (m) | 520 ± 119 (h), 2650 ± 560 (m) | 59.0 ± 17.8 (h), 29.5 ± 0.6 (m) | $5HT_{2B}$ 1.57 |
| 37 | norbornyl | Cl | NH(CH₂)₂OH | 17.6 ± 5.3 (h), 1.56 ± 0.09 (m) | 5400[i] (h), 23 ± 1% (m) | 127 ± 29 (h), 447 ± 43 (m) | $5HT_{2B}$ 0.718, KOR, 2.63 |

Compound 33

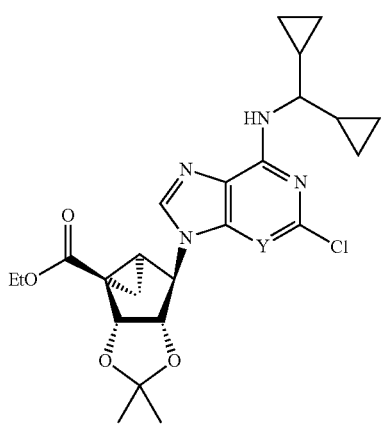

*Ribavirin structure:

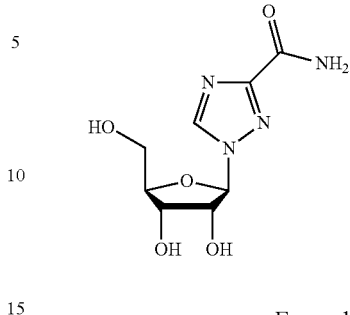

TABLE 6

Purine Methanocarba Analogs

| Cmpd | R[1] | $A_1AR$ % inhibition or $K_i$ (nM)[a] | $A_{2A}AR$ % inhibition[a] | $A_3AR$ % inhibition or $K_i$ (nM)[a] | Off-target, receptor (h, unless noted) ($K_i$, μM)[a] |
|---|---|---|---|---|---|
| 38[g]* (ribavirin) | — | 7410 ± 100 (h) | 23 ± 6% (h) | 16 ± 5% (h) | ND |
| 39 | OMe | 6 ± 4% (h), 2990 ± 80 (m) | 14 ± 5% (h) | 22 ± 4% (h), 15 ± 2% (m) | $β_3$ 1.42, $H_3$ 4.52, $σ_2$ 1.72 |
| 40 | $NH_2$ | 495 ± 35 (h), 25.2 ± 2.8 (m) | 11 ± 3% (h) | 41 ± 6% (h), 47 ± 2% (m) | $5HT_{2B}$ 1.91, $5HT_{2C}$ 2.35, DAT 6.61, $σ_2$ 2.09 |

Example 3

This example demonstrates the functional activity of selected nucleoside derivatives (% $E_{max}$ at 10 μM) at $mA_1AR$ and $mA_3AR$ in a guanine nucleotide binding assay.

cLogP was calculated using ChemDraw Professional, v. 16.0. Binding selectivity for mA1Ar is expressed in terms of fold, compared to $mA_3AR$ (Data from Table 1). $E_{max}$ at the mA3AR is expressed as the mean (effect of 10 μM of test compound as a % of 10 μM 16)±SEM in increasing AR-mediated [$^{35}$S]GTPγS binding, n=3-6. ND, not determined.

TABLE 7

Guanine Nucleotide Binding Assay

| Compound (MW, cLogP) | Binding $K_i$ (and selectivity) for $mA_1AR$ | $E_{max}$, $mA_1AR$, %[c] | $E_{max}$, $mA_3AR$, % |
|---|---|---|---|
| 9 (389, −7.70) | 0.37 nM (2420) | 101 ± 7 | 70 ± 9 |
| 12 (424, −0.39) | 0.65 nM (1000) | 90 ± 19 | 63 ± 5 |
| 24 (400, −7.62) | 0.53 nM (1730) | 97 ± 11 | 92 ± 3 |
| 29 (406, 1.18) | 1.05 nM (547) | 104 ± 6 | 62 ± 5 |
| 31 (424, 2.38) | 1.86 nM (270) | 123 ± 16 | 50 ± 11 |
| 40 (254, −4.52) | 25.2 nM (−400) | ND | 31 ± 3 |

Example 4

This example demonstrates hypothermia and locomotor activity parameters in wild-type C57BL/6J mice.

Compounds were dosed ip. Tb and activity were measured by telemetry and the averages from dosing to 60 min were calculated. P value >0.05 was considered not significant (ns). Data are for the highest dose used and are mean±SD from 3 to 22 mice/group (usually 5-7). P values are unpaired t-Test vs vehicle-treated controls assayed simultaneously. Vehicle data are mean±SD from all (n=83) vehicle treated mice.

TABLE 8

Hypothermia and Locomotor Activity Parameters

| Compound | Dose (mg/kg) | Tb (° C.) | Tb P value | Activity (counts) | Activity P value | ARs causing hypothermia |
|---|---|---|---|---|---|---|
| Vehicle | | 36.3 ± 0.8 | | 15.5 ± 5.5 | | |
| 1 | 1 | 32.4 ± 0.5 | <0.0001 | 1.5 ± 0.5 | 0.0078 | $A_3AR > A_1AR^{30}$ |
| 4 | 3 | 32.2 ± 1.3 | 0.0014 | 2.8 ± 1.6 | 0.0055 | $A_1AR > A_3AR^{30}$ |
| 7 | 3 | 33.4 ± 1.7 | <0.0001 | 5.5 ± 4.1 | <0.0001 | $A_3AR \gg A_1AR^{30}$ |

TABLE 8-continued

Hypothermia and Locomotor Activity Parameters

| Compound | Dose (mg/kg) | Tb (° C.) | Tb P value | Activity (counts) | Activity P value | ARs causing hypothermia |
|---|---|---|---|---|---|---|
| 9 | 3 | 33.0 ± 0.7 | <0.0001 | 6.6 ± 2.3 | <0.0001 | $A_1AR$ selective (FIG. 2) |
| 10 | 10 | 35.8 ± 0.1 | ns | 20.5 ± 4.6 | ns | |
| 12 | 3 | 35.5 ± 0.8 | 0.047 | 13.5 ± 3.5 | ns | |
| 24 | 3 | 36.2 ± 0.4 | ns | 18.1 ± 6.8 | ns | |
| 25 | 10 | 36.6 ± 0.2 | ns | 18.4 ± 3.2 | ns | |
| 26 | 3 | 35.9 ± 0.5 | ns | 14.8 ± 1.7 | 0.041 | |
| 27 | 10 | 36.5 ± 0.6 | ns | 18.9 ± 10.2 | ns | |
| 29 | 3 | 33.4 ± 0.7 | <0.0001 | 10.0 ± 4.3 | 0.046 | $A_3AR > A_1AR$ |
| 31 | 3 | 36.6 ± 0.5 | 0.055 | 16.8 ± 3.6 | 0.040 | |
| 40 | 10 | 35.7 ± 0.7 | ns | 19.1 ± 5.3 | ns | |

Example 5

This example demonstrates plasma protein binding at 10 µM in three species.

Plasma protein binding in human plasma, mouse plasma, and rat plasma was determined. Verapamil and warfarin served as positive controls. The results are expressed as unbound percent±standard deviation. For compound 40, the plasma protein binding was estimated as >80% free. The results are set forth in Table 9.

TABLE 9

Plasma Protein Binding

| Compound | human, % free[b] | mouse, % free[b] | rat, % free[b] |
|---|---|---|---|
| 9 | 6.05 ± 1.60 | 20.6 ± 1.2 | 14.6 ± 0.01 |
| 12 | 5.81 ± 0.39 | 4.74 ± 0.67 | 4.64 ± 0.06 |
| 24 | 14.6 ± 1.3 | 27.5 ± 1.7 | 17.8 ± 1.2 |
| 29 | 9.75 ± 2.03 | 7.68 ± 0.39 | 6.59 ± 0.49 |
| 31 | 4.04 ± 0.60 | 2.95 ± 0.84 | 2.53 ± 0.45 |
| 40 | c | c | c |

Example 6

This example demonstrates the average core body temperature (Tb) of mice dosed with compounds 9 and 24, in accordance with an aspect of the invention.

Mice were dosed with 0.052 mg/kg and with 0.157 mg/kg of compounds 9 and 24. The average Tb was measured after 120 min. The results are shown in FIG. 3.

Figure 3:
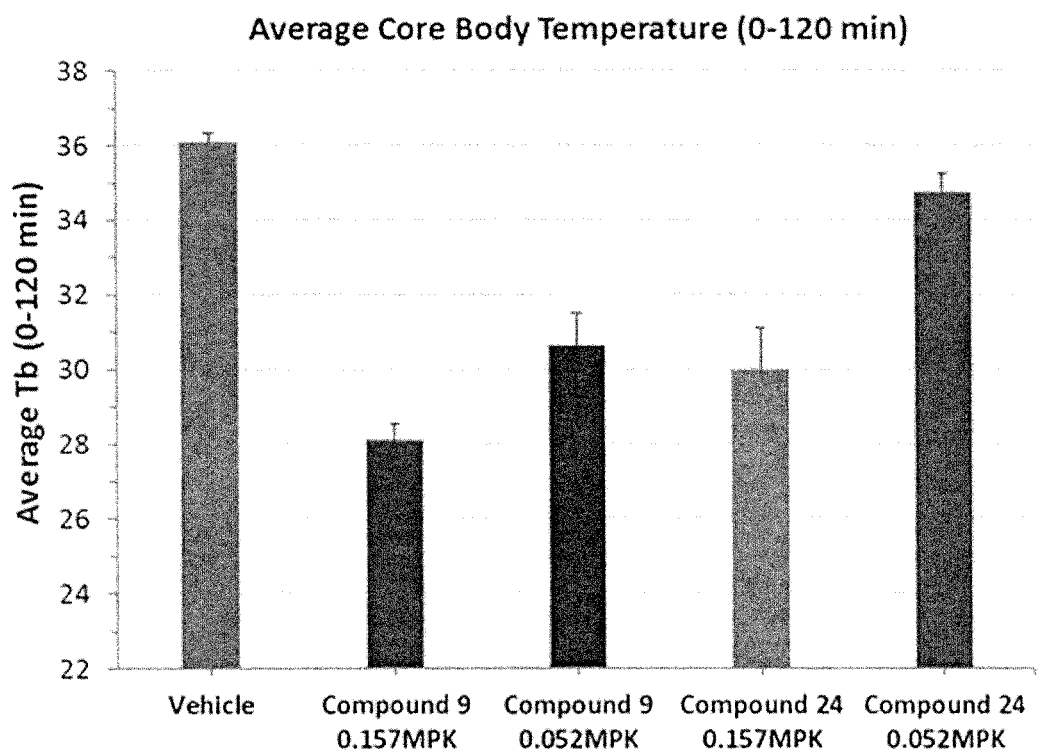

As is apparent from the results shown in FIG. 3, administration of compounds 9 and 24 resulted in robust decreases in Tb in mice after 120 min.

Example 7

This example demonstrates the effect of compound 12 on the immobility time exhibited by mice in the tail suspension test as compared with fluoxetine, a known anti-depressant drug, in accordance with an aspect of the invention.

A first set of five groups of 8 mice were treated with saline (control), or treated with 10 mg/kg of fluoxetine, 0.3 mg/kg of compound 12, 1 mg/kg of compound 12, or 2 mg/kg of compound 12 by i.p. administration. 1 hour after administration of compounds, the mice were individually suspended by their tails for 6 minutes, and the average amount of time the mice were immobile was determined. The immobility times are set forth in FIG. 4A. A second set of five groups of 8 mice were untreated (control), or treated with 10 mg/kg of fluoxetine, 3 mg/kg of comparative compound MRS5474, 10 mg/kg of compound MRS5474, or 20 mg/kg of compound MRS5474 by i.p. administration. 1 hour after administration of compounds, the mice were individually suspended by their tails for 6 minutes, and the average amount of time the mice were immobile was determined. The immobility times are set forth in FIG. 4B. The structure of compound MRS5474 is shown in FIG. 4C.

Figure 4A:
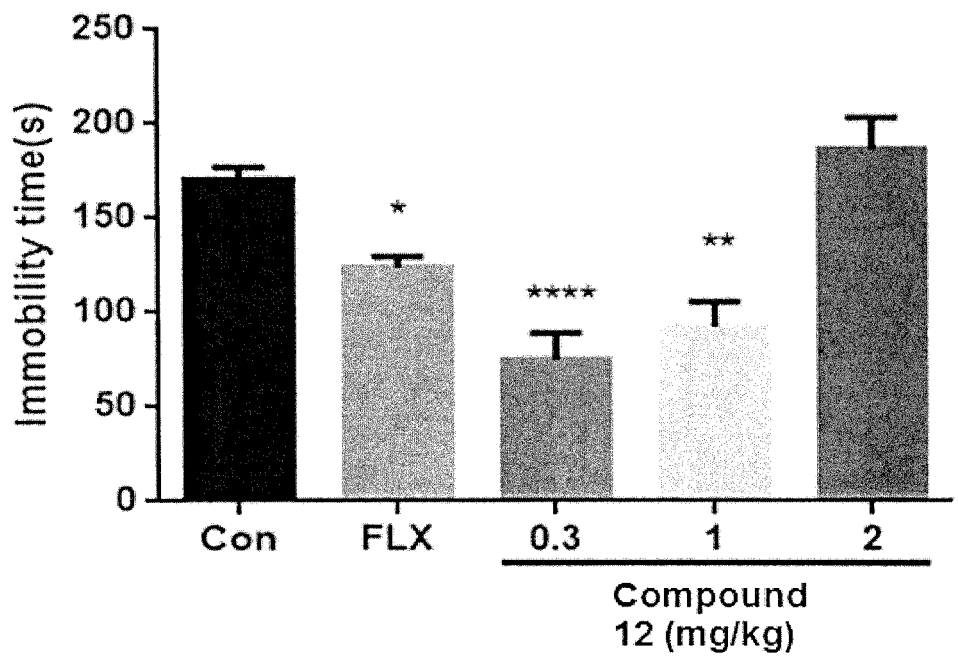
FIG. 4B shows the average immobility time in the tail suspension test exhibited by mice treated i.p. with saline (control), 10 mg/kg fluoxetine (FLX), or 3 mg/kg of compound MRS5474, 10 mg/kg of compound MRS5474, or 20 mg/kg of compound MRS5474.
FIG. 4C shows the structure of MRS5474.
Figure 4B:
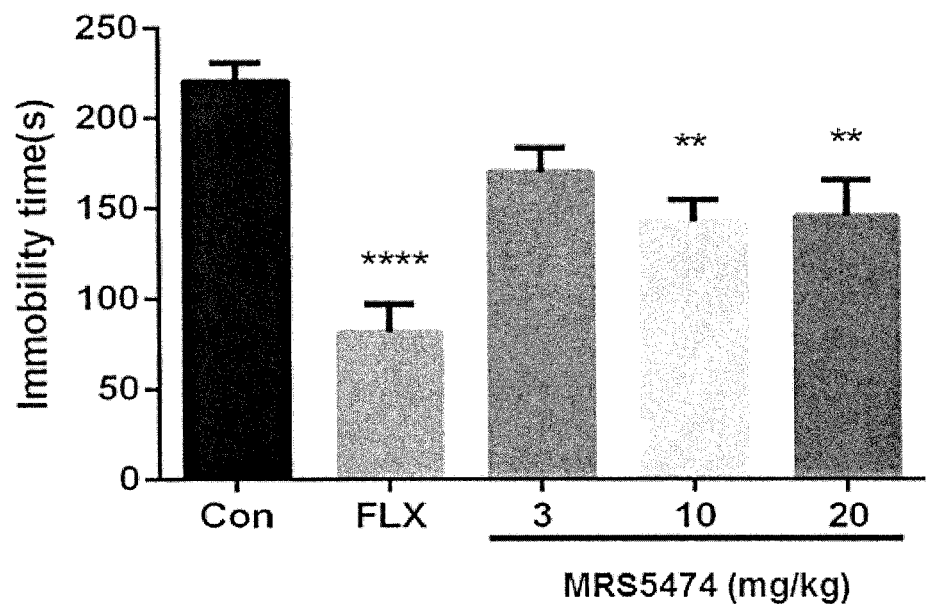
Figure 4C:
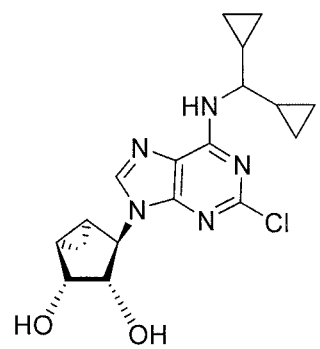

As is apparent from the results shown in FIGS. 4A and 4B, mice treated with 0.3 mg/kg of compound 12 exhibited an average immobility time in the tail suspension test that was approximately ⅔ of the average immobility time exhibited by mice treated with 10 mg/kg of fluoxetine, and approximately ½ of the average immobility time exhibited by the control group of mice. Mice treated with 3 mg/kg, 10 gm/kg, or 20 mg/kg of MRS5474 exhibited average immobility times that were lower than the average immobility times exhibited by the control group of mice, but were approximately twice longer than the average immobility times exhibited by mice treated with fluoxetine.

Example 8

This example demonstrates the stability of compound 12 in simulated gastric fluid, in accordance with an aspect of the invention.

Compound 12 and MRS5474 (comparative) were kept in simulated gastric fluid at a pH of 1.60 and a temperature of 37° C. After 120 min, 100% of the initial amount of compound 12 was present in the fluid while 51% of the initial amount of MRS5474 was present in the fluid.

REFERENCES 1. a) Kiesman W. F.; Elzein, E.; Zablocki, J. $A_1$ Adenosine receptor antagonists, agonists, and allosteric enhancers. C. N. Wilson and S. J. Mustafa (eds.), Adenosine Receptors in Health and Disease, Handbook of Experimental Pharmacology 2009, 193, 25-58. b) Schenone, S.; Brullo, C.; Musumeci, F.; Bruno, O.; Botta, M. $A_1$ receptors ligands: past, present and future trends. Curr. Top. Med. Chem. 2010, 10, 878-901. c) Giorgi, I.; Nieri, P. Adenosine A, modulators: a patent update (2008 to present). Exp. Opin. Therap. Patents 2013, 23, 1109-1121.
2. Gao, Z. G.; Tosh, D. K.; Jain, S.; Yu, J.; Suresh, R. R.; Jacobson, K. A. Chapter 4. $A_1$ adenosine receptor agonists, antagonists, and allosteric modulators. In: The Adenosine Receptors, Varani, K. (ed.). Springer, 2018, 34, 59-89, DOI: 10.1007/978-3-319-90808-3_4.

3. Luongo, L.; Petrelli, R.; Gatta, L.; Giordano, C.; Guida, F.; Vita, P.; Franchetti, P.; Grifantini, M.; Novellis, V. D.; Cappellacci, L.; Maione, S. 5'-Chloro-5'-deoxy-(±)-ENBA, a potent and selective adenosine $A_1$ receptor agonist, alleviates neuropathic pain in mice through functional glial and microglial changes without affecting motor or cardiovascular functions. *Molecules* 2012, 17, 13712-13726.
4. Knutsen, L. J. S.; Lau, J.; Petersen, H.; Thomsen, C.; Weis, J. U.; Shalmi, M.; Judge, M. E.; Hansen, A. J.; Sheardown, M. J. N-Substituted adenosines as novel neuroprotective $A_1$ agonists with diminished hypotensive effects. *J. Med. Chem.* 1999, 42, 3463-3477
5. Schulte, G.; Sommerschild, H.; Yang, J.; Tokuno, S.; Goiny, M.; Lövdahl, C.; Johansson, B.; Fredholm, B. B.; Valen, G. Adenosine $A_1$ receptors are necessary for protection of the murine heart by remote, delayed adaptation to ischaemia. *Acta Physiol. Scand.* 2004, 182, 133-143.
6. Serchov, T.; Clement, H. W.; Schwartz, M. K.; Iasevoli, F.; Tosh, D. K.; Idzko, M.; Jacobson, K. A.; de Bartolomeis, A.; Normann, C.; Biber, K.; van Calker, D. Increased signaling via adenosine $A_1$ receptors, sleep deprivation, imipramine, and ketamine inhibit depressive-like behavior via induction of Homer1a. *Neuron* 2015, 87, 549-562.
7. a) Boison, D. Adenosine as a neuromodulator in neurological diseases. *Curr. Opin. Pharmacol.* 2008, 8, 2-7. b) Greene, R. W.; Bjorness, T. E.; Suzuki, A. The adenosine-mediated, neuronal-glial, homeostatic sleep response. *Curr. Opin. Neurobiol.* 2017, 44, 236-242.
8. Petrelli, R.; Scortichini, M.; Kachler, S.; Boccella, S.; Cerchia, C.; Torquati, I.; Del Bello, F.; Salvemini, D.; Novellino, E.; Luongo, L.; Maione, S.; Jacobson, K.; Lavecchia, A.; Klotz, K. N.; Cappellacci, L. Exploring the role of $N^6$-substituents in potent dual acting 5'-C-ethyl-tetrazolyl-adenosine derivatives: synthesis, binding, functional assays and antinociceptive effects in mice. *J. Med. Chem.* 2017, 60, 4327-4341.
9. Sawynok, J. Adenosine receptor targets for pain. *Neuroscience* 2016, 338:1-18.
10. a) Tozzi, M.; Novak, I. Purinergic receptors in adipose tissue as potential targets in metabolic disorders. *Front Pharmacol.* 2017, 8, 878. b) Merkel, L. A.; Hawkins, E. D.; Colussi, D. J.; Greenland, B. D.; Smits, G. J.; Perrone, M. H.; Cox, B. F. Cardiovascular and antilipolytic effects of the adenosine agonist GR79236. *Pharmacology* 1995, 51, 224-236.
11. Mor, M.; Shalev, A.; Dror, S.; Pikovsky, O.; Beharier, O.; Moran, A.; Katz, A.; Etzion, Y. INO-8875, a highly-selective $A_1$ adenosine receptor agonist: Evaluation of chronotropic, dromotropic and hemodynamic effects in rats. *J. Pharmacol. Exp. Therap.* 2010, Retrieved from http://jpet.aspetjournals.org/content/early/2010/05/21/jpet.110.169383.abstract
12. Tupone, D.; Madden, C. J.; Morrison, S. F. Central activation of the $A_1$ adenosine receptor ($A_1AR$) induces a hypothermic, torpor-like state in the rat. *J. Neurosci.* 2013, 33, 14512-14525.
13. Jinka, T. R.; Combs, V. M.; Drew, K. L. Translating drug-induced hibernation to therapeutic hypothermia. *ACS Chem. Neurosci.* 2015, 6, 899-904.
14. Carlin, J. L.; Jain, S.; Gizewski, E.; Wan, T. C.; Tosh, D. K.; Xiao, C.; Auchampach, J. A.; Jacobson, K. A.; Gavrilova, O.; Reitman, M. L. Hypothermia in mouse is caused by adenosine $A_1$ and $A_3$ receptor agonists and AMP via three distinct mechanisms. *Neuropharmacology* 2017, 114, 101-113.
15. Jacobson, K. A.; Gao, Z. G.; Tchilibon, S.; Duong, H. T.; Joshi, B. V.; Sonin, D.; Liang, B. T. Semirational design of (N)-methanocarba nucleosides as dual acting $A_1$ and $A_3$ adenosine receptor agonists: Novel prototypes for cardioprotection. *J. Med. Chem.* 2005, 48, 8103-8107.
16. Tosh, D. K.; Ciancetta, A.; Warnick, E.; Crane, S.; Gao, Z. G.; Jacobson, K. A. Structure-based scaffold repurposing for G protein-coupled receptors: Transformation of adenosine derivatives into $5HT_{2B}/5HT_{2C}$ serotonin receptor antagonists. *J. Med. Chem.* 2016, 59, 11006-11026.
17. Müller, C. E.; Jacobson, K. A. Recent developments in adenosine receptor ligands and their potential as novel drugs. *Biochim. Biophys. Acta—Biomembranes* 2011, 1808, 1290-1308.
18. Rodriguez, D.; Chakraborty, S.; Warnick, E.; Crane, S.; Gao, Z. G.; O'Connor, R. O.; Jacobson, K. A.; Carlsson, J. Structure-based screening of uncharted chemical space for atypical adenosine receptor agonists. *ACS Chem. Biol.* 2016, 11, 2763-2772.
19. van der Hoeven, D.; Wan, T. C.; Gizewski, E. T.; Kreckler, L. M.; Maas, J. E.; Van Orman, J.; Ravid, K.; Auchampach, J. A. A role for the low-affinity $A_{2B}$ adenosine receptor in regulating superoxide generation by murine neutrophils. *J. Pharmacol. Exp. Therap.* 2011, 338, 1004-1012.
20. Jacobson, K. A.; Ohno, M.; Duong, H. T.; Kim, S. K.; Tchilibon, S.; Cesnek, M.; Holy, A.; Gao, Z. G. A neoceptor approach to unraveling microscopic interactions between the human $A_{2A}$ adenosine receptor and its agonists. *Chemistry and Biology* 2005, 12, 237-247.
21. Gao, Z. G.; Blaustein, J.; Gross, A. S.; Melman, N.; Jacobson, K. A. $N^6$—Substituted adenosine derivatives: Selectivity, efficacy, and species differences at $A_3$ adenosine receptors. *Biochem. Pharmacol.* 2003, 65, 1675-1684.
22. Tosh, D. K.; Phan, K.; Gao, Z. G.; Gakh, A.; Xu, F.; Deflorian, F.; Abagyan, R.; Stevens, R. C.; Jacobson, K. A.; Katritch, V. Optimization of adenosine 5'-carboxamide derivatives as adenosine receptor agonists using structure-based ligand design and fragment-based searching. *J. Med. Chem.* 2012, 55, 4297-4308.
23. Gallo-Rodriguez, C.; Ji, X.-D.; Melman, N.; Siegman, B. D.; Sanders, L. H.; Orlina, J.; Fischer, B.; Pu, Q.-L.; Olah, M. E.; van Galen, P. J. M.; Stiles, G. L.; Jacobson, K. A. Structure-activity relationships of $N^6$-benzyladenosine-5'-uronamides as $A_3$-selective adenosine agonists. *J. Med. Chem.* 1994, 37, 636-646.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of formula (I), (II), or (III):

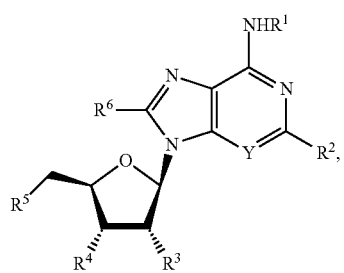

(I)

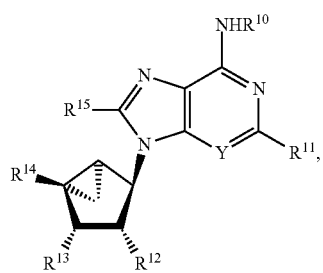

(II)

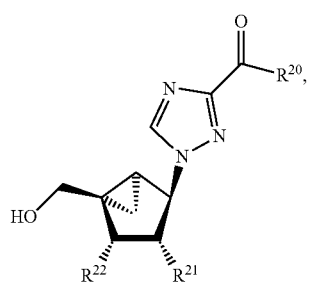

(III)

wherein:
in formula (I):
Y is N or CH,
$R^1$ is dicyclobutylmethyl, dicyclopentylmethyl, dicyclohexylmethyl, dicycloheptylmethyl, dicyclooctylmethyl, dicyclononylmethyl, or dicyclodecylmethyl,
$R^2$ and $R^6$ are independently selected from hydrogen, halo, $C_1$-$C_6$ alkyl, $C_2$-$C_6$ alkenyl, $C_2$-$C_6$ alkynyl, heteroaryl, $C_1$-$C_6$ alkylthio, $C_1$-$C_6$ alkoxy, and $C_1$-$C_6$ alkylamino;
$R^3$ and $R^4$ are independently selected from hydrogen, hydroxyl, amino, mercapto, ureido, $C_1$-$C_6$ alkyl carbonylamino, hydroxy $C_1$-$C_6$ alkyl, and hydrazinyl; and
$R^5$ is selected from hydrogen, hydroxyl, halo, $C_1$-$C_3$ alkyl aminocarbonyl, hydroxy $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;
in formula (II):
Y is N or CH,
$R^{10}$ is dicyclobutylmethyl, dicyclopentylmethyl, dicyclohexylmethyl, dicycloheptylmethyl, dicyclooctylmethyl, dicyclononylmethyl, dicyclodecylmethyl, or endo-2-norbornyl,
$R^{11}$ and $R^{15}$ are independently selected from hydrogen, halo, $C_1$-$C_6$ alkyl, $C_2$-$C_6$ alkenyl, $C_2$-$C_6$ alkynyl, heteroaryl, $C_1$-$C_6$ alkylthio, $C_1$-$C_6$ alkoxy, and $C_1$-$C_6$ alkylamino;
$R^{12}$ and $R^{13}$ are independently selected from hydrogen, hydroxyl, amino, mercapto, ureido, $C_1$-$C_6$ alkyl carbonylamino, hydroxy $C_1$-$C_6$ alkyl, and hydrazinyl; and
$R^{14}$ is selected from hydrogen, $C_1$-$C_3$ alkoxycarbonyl, $C_1$-$C_3$ alkyl aminocarbonyl, hydroxy $C_1$-$C_3$ alkyl aminocarbonyl, di($C_1$-$C_3$ alkyl) aminocarbonyl, $C_3$-$C_8$ cycloalkyl aminocarbonyl, $C_1$-$C_3$ alkylthio $C_1$-$C_3$ alkyl, $C_6$-$C_{10}$ arylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl, wherein the aryl portion is optionally substituted with one or more substituents selected from halo and $C_1$-$C_3$ alkoxy;
with the proviso that when $R^{11}$ is chloro and $R^{14}$ is hydrogen, $R^{10}$ is not dicyclopentylmethyl; and
in formula (III),
$R^{20}$ is amino, $C_1$-$C_3$ alkoxy, $C_1$-$C_3$ alkylamino, hydroxy $C_1$-$C_3$ alkylamino, di($C_1$-$C_3$ alkyl)amino, or $C_3$-$C_8$ cycloalkylamino, and
$R^{21}$ and $R^{22}$ are independently selected from hydrogen, hydroxyl, amino, mercapto, ureido, $C_1$-$C_6$ alkyl carbonylamino, hydroxy $C_1$-$C_6$ alkyl, and hydrazinyl;
or a pharmaceutically acceptable salt thereof.

2. The compound or salt of claim 1, wherein the compound is a compound of formula (I).

3. The compound or salt of claim 2, wherein $R^6$ is hydrogen.

4. The compound or salt of claim 2, wherein Y is N.

5. The compound or salt of claim 2, wherein $R^3$ and $R^4$ are both hydroxyl.

6. The compound or salt of claim 2, wherein $R^5$ is selected from hydroxyl and halo.

7. The compound or salt of claim 2, wherein $R^2$ is H or chloro.

8. The compound or salt of claim 2, wherein the compound is:

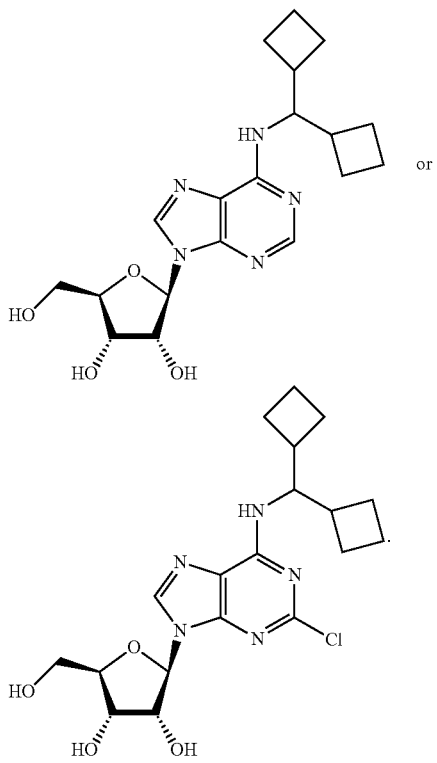 or 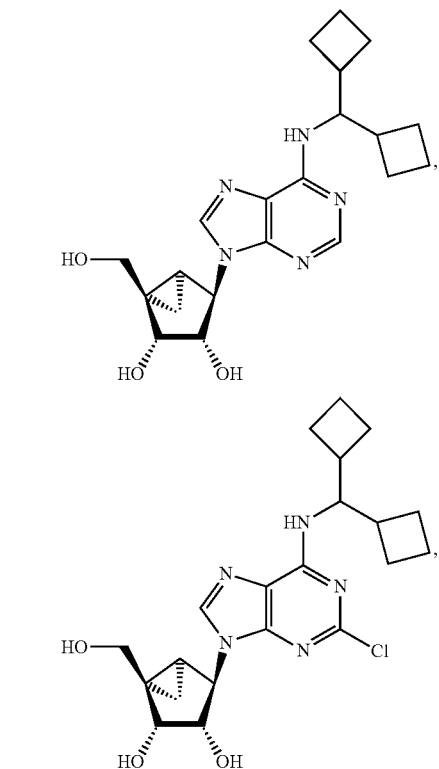

9. The compound or salt of claim 1, wherein the compound is of formula (II).

10. The compound or salt of claim 9, wherein $R^{15}$ is hydrogen.

11. The compound or salt of claim 9, wherein Y is N.

12. The compound or salt of claim 9, wherein $R^{12}$ and $R^{13}$ are both hydroxyl.

13. The compound or salt of claim 9, wherein $R^{11}$ is H or chloro.

14. The compound or salt of claim 9, wherein $R^{14}$ is H.

15. The compound or salt of claim 14, wherein the compound is:

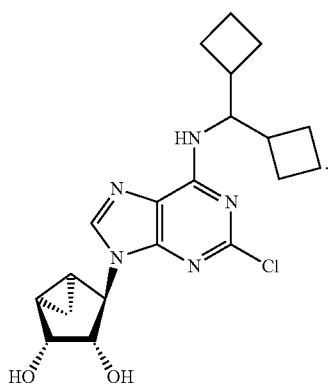

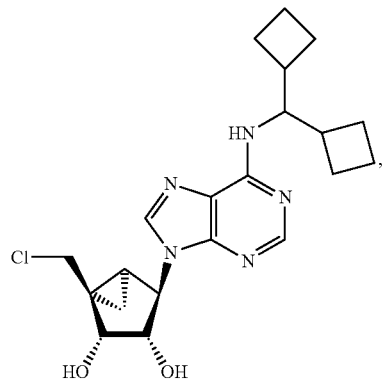

16. The compound or salt of claim 9, wherein $R^{14}$ is halo $C_1$-$C_3$ alkyl or hydroxy $C_1$-$C_3$ alkyl.

17. The compound or salt of claim 16, wherein the compound is selected from:

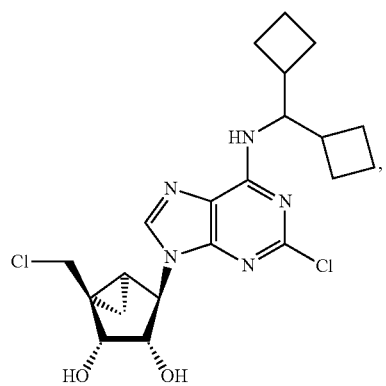

63
-continued

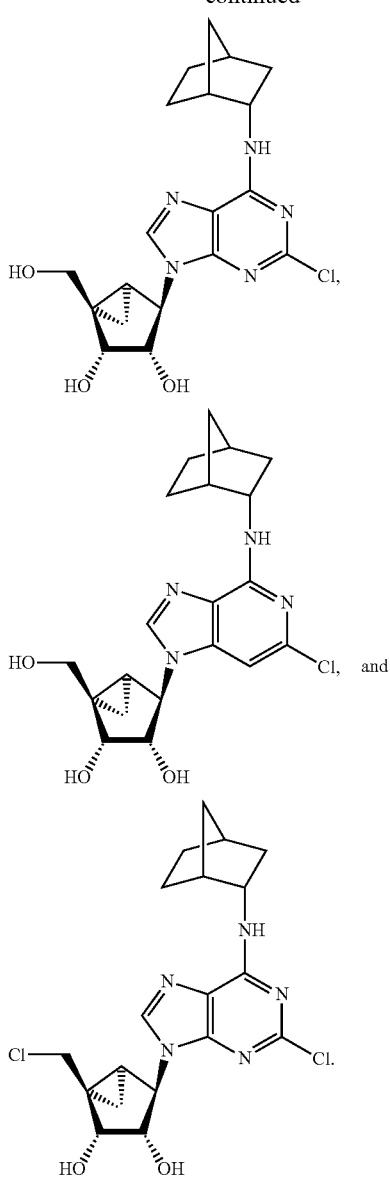

18. The compound or salt of claim 1, wherein the compound is a compound of formula (III).

19. The compound or salt of claim 18, wherein $R^{21}$ and $R^{22}$ are both hydroxyl.

20. The compound or salt of claim 19, wherein the compound is:

64

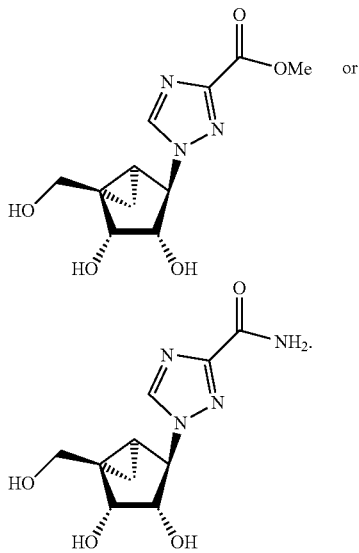

21. A pharmaceutical composition comprising a compound or salt of claim 1 and a pharmaceutically acceptable carrier.

22. A method of inducing and/or maintaining a hypothermic and/or hypometabolic state in a mammal in need thereof comprising administering an effective amount of a compound or salt of claim 1.

23. The method of claim 22, wherein the mammal has been afflicted with at least one of an anoxic, hypoxic, or hypoperfusion event.

24. The method of claim 22, wherein the anoxic, hypoxic, or hypoperfusion event is selected from birth injury, cardiac arrhythmia, heart attack, cardiac arrest, stroke, brain injury, trauma, and head injury.

25. The method of claim 22, wherein the mammal is subjected to a surgical procedure.

26. The method of claim 25, wherein the compound or salt thereof is administered before, during, or after the surgical procedure.

27. The method of claim 22, wherein the compound or salt is administered as an intrathecal, oral, or parenteral composition.

28. A method of treating a disease or disorder in a mammal in need thereof comprising administering an effective amount of a compound or salt of claim 1, wherein the disease or disorder is selected from chronic pain, acute pain, diabetes, cardiac arrhythmia, myocardial infarction, depression, and brain ischemia.

29. The method of claim 28, wherein the compound or salt is administered as an intrathecal, oral, or parenteral composition.

* * * * *